(12) United States Patent
Ludwig et al.

(10) Patent No.: US 11,337,829 B2
(45) Date of Patent: May 24, 2022

(54) DEVICES FOR INSERTING AND EXPANDING SPINAL IMPLANTS

(71) Applicant: K2M, Inc., Leesburg, VA (US)

(72) Inventors: Steven Ludwig, Baltimore, MD (US); Scott Dhupar, Windsor, CO (US); Sabatino Bianco, Arlington, TX (US); Khalid Abbed, New Haven, CT (US); Egon Doppenberg, Lake Bluff, IL (US); Jennifer Moore, Leesburg, VA (US); John Donohoe, Morrisville, NC (US); Scott A. Jones, Mcmurray, PA (US); Todd Wallenstein, Ashburn, VA (US); Brad Vinckier, Leesburg, VA (US); Jordan Floyd, Westlake, OH (US); Gregory Lanford, Nashville, TN (US); Brian O'Shaughnessy, Nashville, TN (US); Thomas Morrison, Atlanta, GA (US)

(73) Assignee: K2M, Inc., Leesburg, VA (US)

( * ) Notice: Subject to any disclaimer, the term of this patent is extended or adjusted under 35 U.S.C. 154(b) by 566 days.

(21) Appl. No.: 16/296,697

(22) Filed: Mar. 8, 2019

(65) Prior Publication Data
US 2019/0274845 A1  Sep. 12, 2019

Related U.S. Application Data

(60) Provisional application No. 62/640,881, filed on Mar. 9, 2018.

(51) Int. Cl.
*A61F 2/46* (2006.01)
*B25B 23/142* (2006.01)
(Continued)

(52) U.S. Cl.
CPC .......... *A61F 2/4611* (2013.01); *B25B 23/142* (2013.01); *A61B 2017/0256* (2013.01); (Continued)

(58) Field of Classification Search
CPC .......... A61F 2/4611; A61F 2/447; A61F 2/46; A61F 2/44; A61F 2/4425; A61F 2/4455; (Continued)

(56) References Cited

U.S. PATENT DOCUMENTS 8,303,663 B2  11/2012 Jimenez et al.
8,438,956 B1   5/2013 Holmes et al.
(Continued)

OTHER PUBLICATIONS

Extended European Search Report including Written Opinion for Application No. EP19161612.7 dated Aug. 5, 2019, pp. 1-7.

*Primary Examiner* — Marcela I. Shirsat
(74) *Attorney, Agent, or Firm* — Lerner, David, Littenberg, Krumholz & Mentlik, LLP

(57) ABSTRACT

A driving instrument for adjusting a spinal implant includes an outer shaft having a distal end configured to actuate a proximal adjustment assembly of a spinal implant, and an inner shaft having a distal end configured to actuate a distal adjustment assembly of the spinal implant. The inner shaft is disposed within the outer shaft, with a proximal end of the inner shaft extending proximally from the outer shaft. The proximal end is configured to be rotated such that rotation of the inner shaft results in simultaneous rotation of the inner and outer shafts, with rotation of the outer shaft ceasing at a first value of resistance associated with the proximal adjustment assembly and rotation of the inner shaft ceasing at a second value of resistance associated with the distal adjustment assembly such that cessation of rotation of the inner shaft is independent from cessation of rotation of the outer shaft.

17 Claims, 22 Drawing Sheets

(51) Int. Cl.
*A61F 2/44* (2006.01)
*A61F 2/30* (2006.01)
*A61B 17/02* (2006.01)

(52) U.S. Cl.
CPC ............ *A61F 2/447* (2013.01); *A61F 2/4425* (2013.01); *A61F 2/4455* (2013.01); *A61F 2002/30556* (2013.01); *A61F 2002/30579* (2013.01); *A61F 2002/4615* (2013.01); *A61F 2002/4625* (2013.01); *A61F 2002/4627* (2013.01)

(58) Field of Classification Search
CPC ............ A61F 2/4465; A61F 2002/4615; A61F 2002/4627; A61F 2002/4628; A61F 2002/30405; A61F 2002/30525; A61F 2002/30556; A61F 2002/30579; A61B 17/7065; A61B 2017/0256
USPC ............................... 623/17.11–17.16; 606/99

See application file for complete search history.

(56) References Cited

U.S. PATENT DOCUMENTS

| | | | |
|---|---|---|---|
| 8,636,746 B2 | 1/2014 | Jimenez et al. | |
| 8,771,360 B2 | 7/2014 | Jimenez et al. | |
| 8,932,302 B2 | 1/2015 | Jimenez et al. | |
| 9,358,125 B2 | 6/2016 | Jimenez et al. | |
| 9,393,130 B2 | 7/2016 | Suddaby et al. | |
| 9,474,626 B2 | 10/2016 | Jimenez et al. | |
| 9,498,270 B2 | 11/2016 | Jimenez et al. | |
| 9,585,762 B2 | 3/2017 | Suddaby et al. | |
| 9,808,352 B2 | 11/2017 | Suddaby et al. | |
| 9,808,353 B2 | 11/2017 | Suddaby et al. | |
| 10,004,608 B2 | 6/2018 | Carnes et al. | |
| 10,117,757 B2 | 11/2018 | Jimenez et al. | |
| 10,159,584 B2 | 12/2018 | Carnes et al. | |
| 10,369,008 B2* | 8/2019 | Jimenez | A61B 17/7065 |
| 2005/0015097 A1 | 1/2005 | Mujwid et al. | |
| 2007/0093850 A1 | 4/2007 | Harris et al. | |
| 2011/0138948 A1* | 6/2011 | Jimenez | F16H 25/2056 74/424.82 |
| 2016/0166396 A1* | 6/2016 | McClintock | A61F 2/30771 623/17.16 |
| 2017/0100258 A1 | 4/2017 | Jimenez et al. | |
| 2017/0258605 A1* | 9/2017 | Blain | A61F 2/4611 |
| 2019/0021868 A1* | 1/2019 | Ludwig | A61F 2/447 |

* cited by examiner

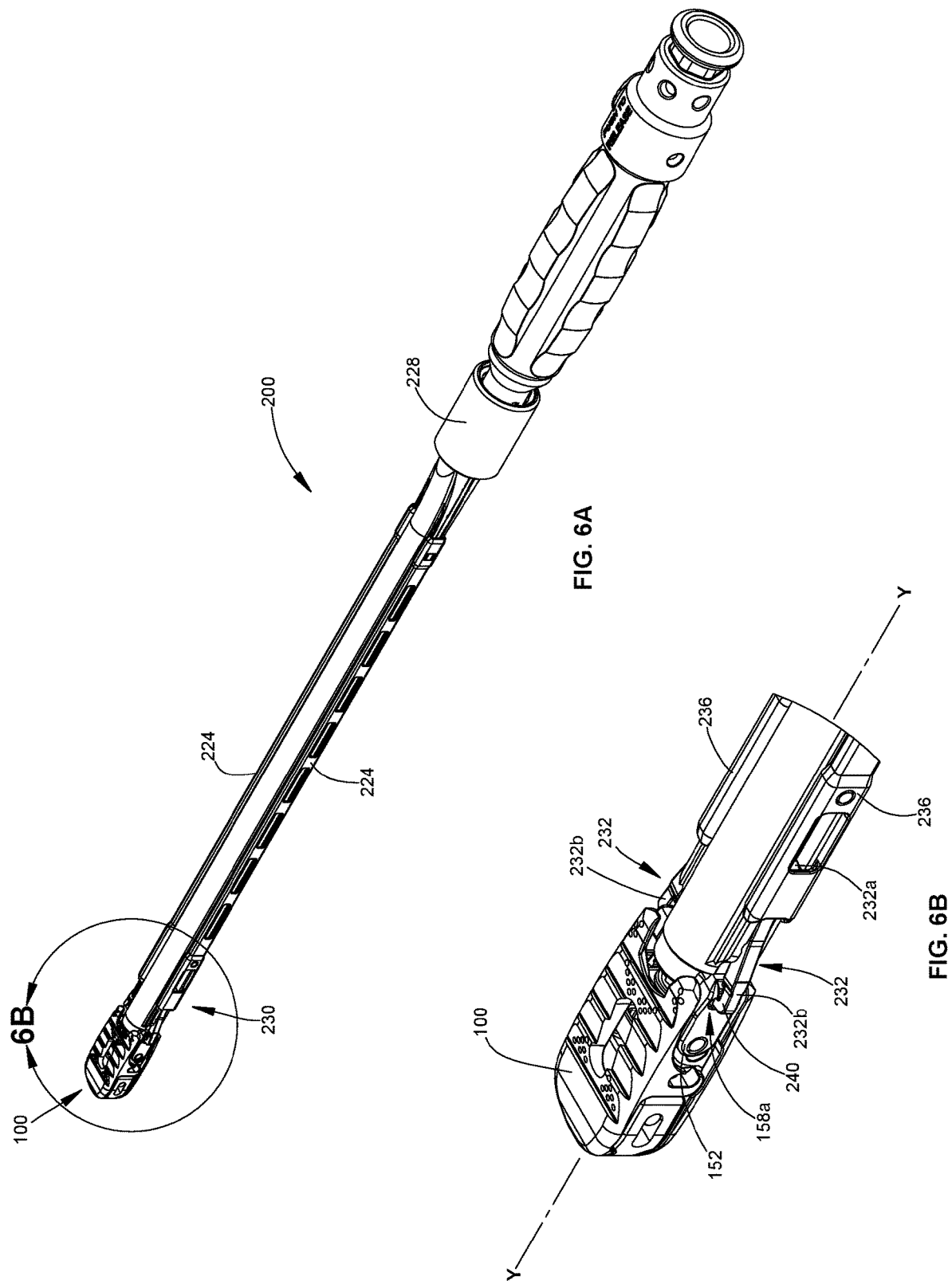

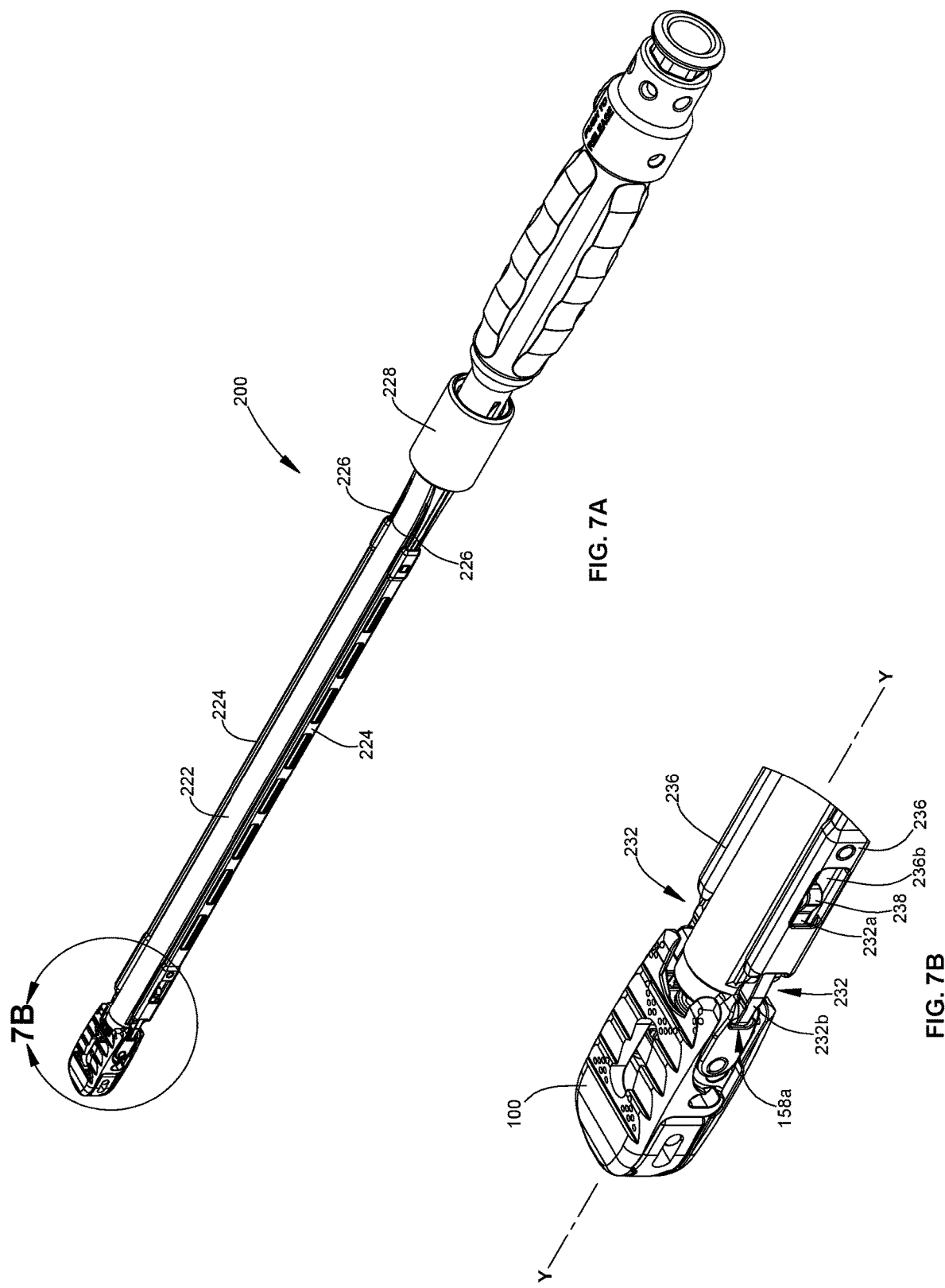

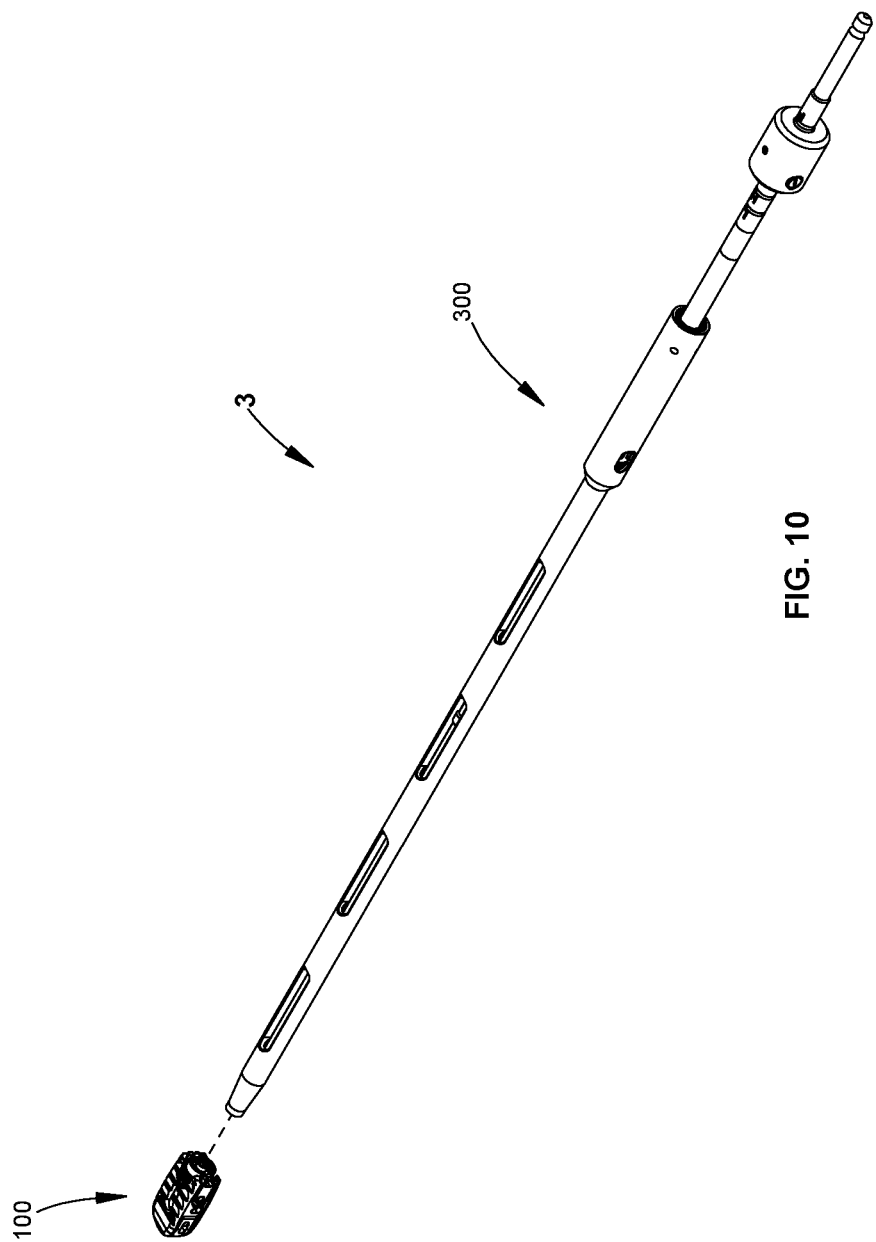

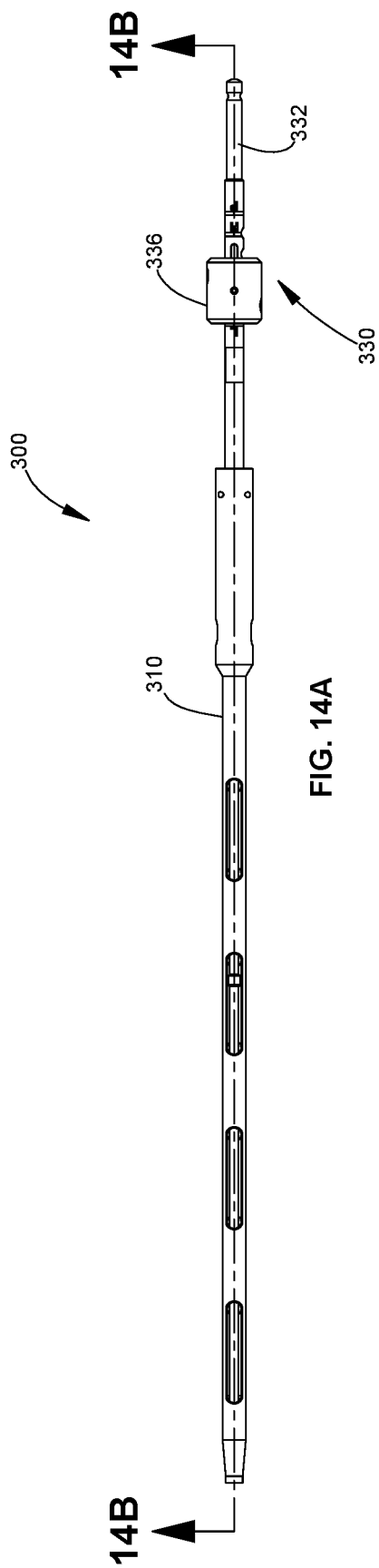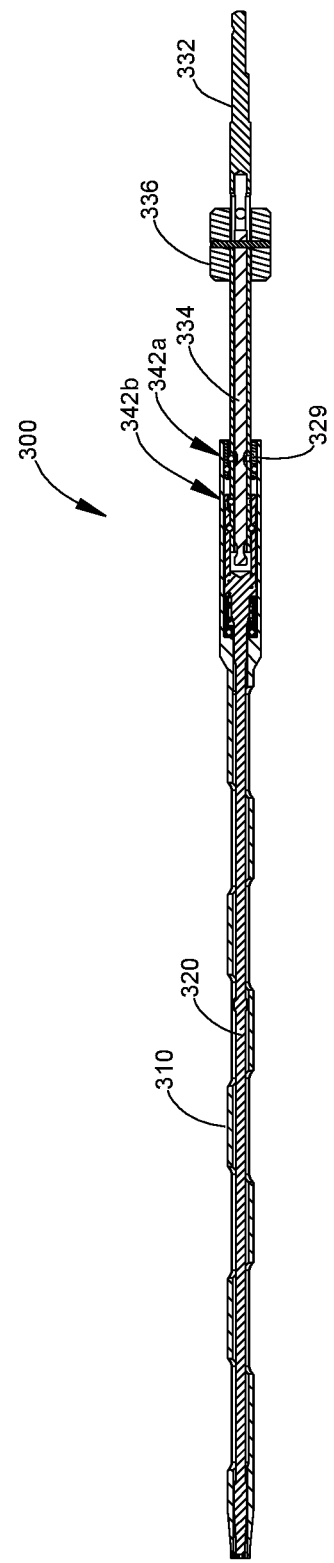
FIG. 14A
FIG. 14B

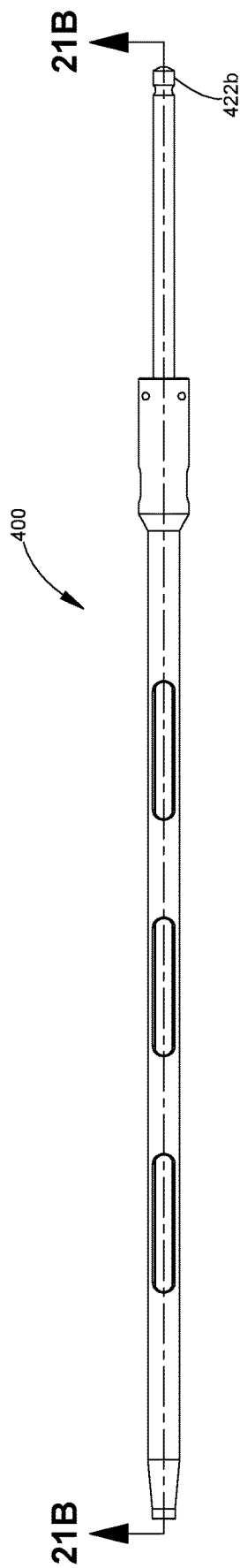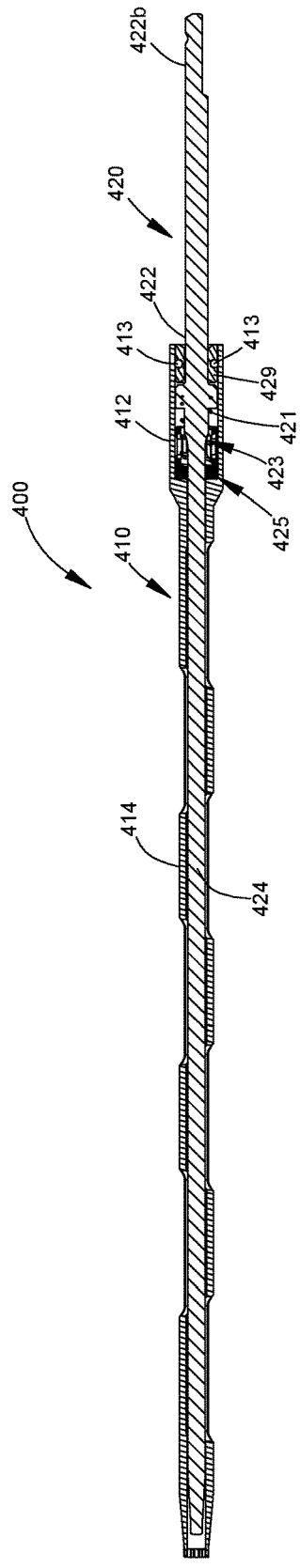
FIG. 21A
FIG. 21B

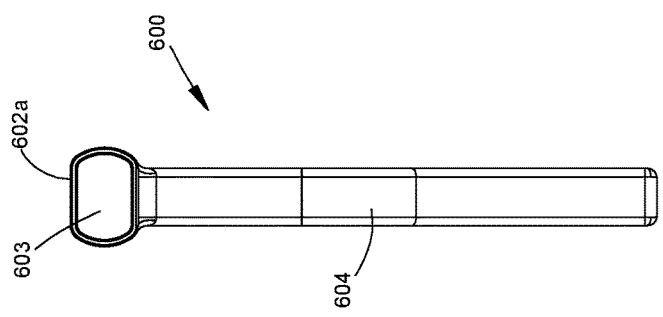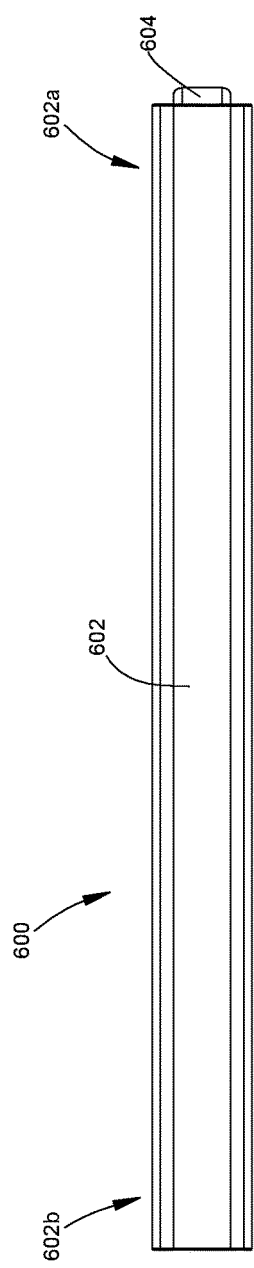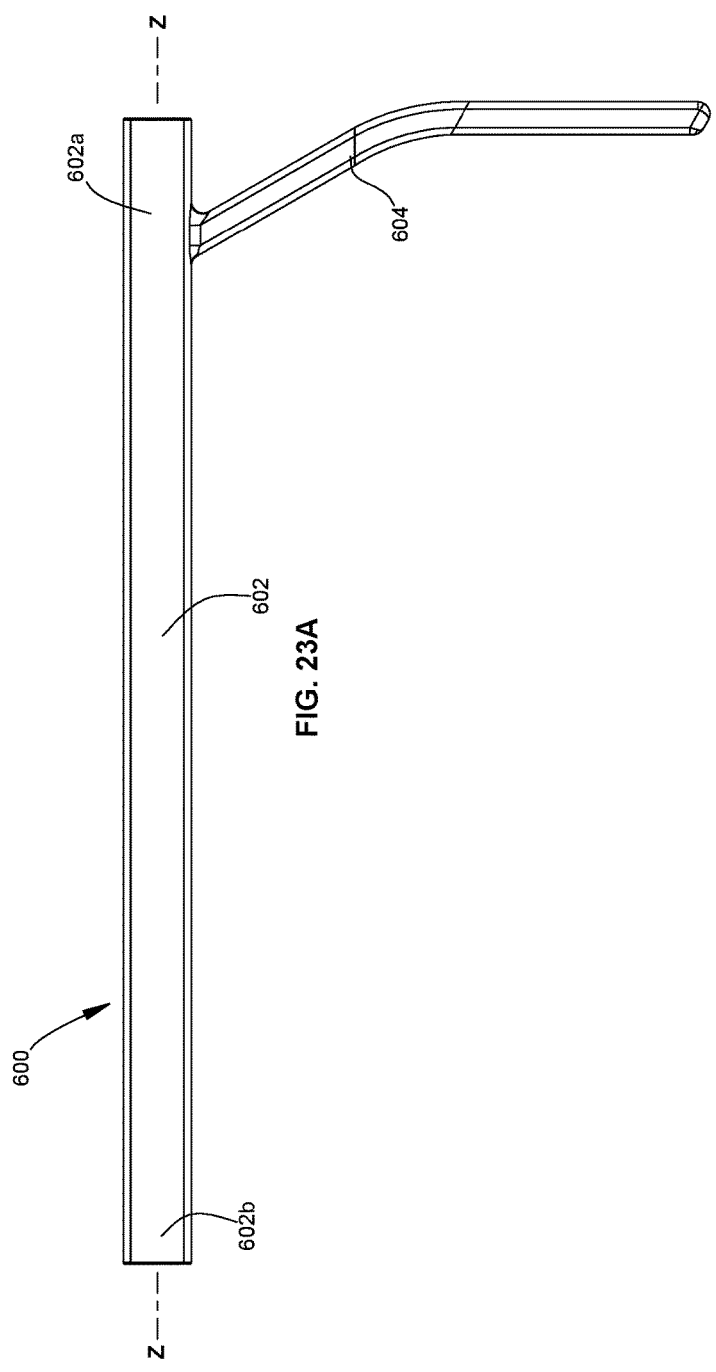
FIG. 23C
FIG. 23B
FIG. 23A

DEVICES FOR INSERTING AND EXPANDING SPINAL IMPLANTS

CROSS-REFERENCE TO RELATED APPLICATIONS

This application claims the benefit of the filing date of United States Provisional Patent Application No. 62/640,881 filed Mar. 9, 2018, the disclosure of which is hereby incorporated herein by reference.

TECHNICAL FIELD

The present disclosure relates generally to orthopedic surgical devices, and more particularly, to devices for inserting, positioning, and/or adjusting expandable spinal implants and methods of using the same.

BACKGROUND

The spinal column is a complex system of bones and connective tissues that provide support for the human body and protection for the spinal cord and nerves. The adult spine includes an upper portion and a lower portion. The upper portion contains twenty-four discrete bones, which are subdivided into three areas including seven cervical vertebrae, twelve thoracic vertebrae, and five lumbar vertebrae. The lower portion includes the sacral and coccygeal bones. The cylindrical shaped bones, called vertebrae or vertebral bodies, progressively increase in size from the upper portion downwards to the lower portion.

An intervertebral disc along with two posterior facet joints cushion and dampen the various translational and rotational forces exerted upon the spinal column. The intervertebral disc is a spacer located between two vertebral bodies. The facets provide stability to the posterior portion of adjacent vertebrae. The spinal cord is housed in the canal of the vertebral bodies. It is protected posteriorly by the lamina. The lamina is a curved surface with three main protrusions. Two transverse processes extend laterally from the lamina, while the spinous process extends caudally and posteriorly. The vertebral bodies and lamina are connected by a bone bridge called the pedicle.

The spine is a flexible structure capable of a large range of motion. There are various disorders, diseases, and types of injury, which restrict the range of motion of the spine or interfere with important elements of the nervous system. The problems include, but are not limited to, scoliosis, kyphosis, excessive lordosis, spondylolisthesis, slipped or ruptured disc, degenerative disc disease, vertebral body fracture, and tumors. Persons suffering from any of the above conditions typically experience extreme and/or debilitating pain, and often times diminished nerve function. These conditions and their treatments can be further complicated if the patient is suffering from osteoporosis, or bone tissue thinning and loss of bone density.

Spinal discs between the endplates of adjacent vertebrae in a spinal column of the human body provide critical support. However, due to injury, degradation, disease, or the like, these discs can rupture, degenerate, and/or protrude to such a degree that the intervertebral space between adjacent vertebrae collapses as the disc loses at least a part of its support function. This can cause impingement of the nerve roots and severe pain.

In some cases, surgical correction may be required. Some surgical corrections include the removal of the natural spinal disc from between the adjacent vertebrae. In order to preserve the intervertebral disc space for proper spinal column function, an interbody spacer can be inserted between the adjacent vertebrae.

Typically, a prosthetic implant is inserted between the adjacent vertebrae and may include pathways that permit bone growth between the adjacent vertebrae until they are fused together. However, there exists a possibility that conventional prosthetic implants may be dislodged or moved from their desired implantation location due to movement by the patient before sufficient bone growth or fusion has occurred. Due to the concave nature of the vertebral body endplates, it can be challenging to obtain enough contact between the implant and the endplates to create bone growth. Additionally, achieving the desired lordosis can be difficult given the limitation of typical prosthetic implants once they are implanted.

Therefore, a need exists for systems that maximize contact of spinal implants with the vertebral body endplates such that a spinal implant matches the desired amount of lordosis, allows for bone growth between adjacent vertebrae, maintains the space between adjacent vertebrae during bone ingrowth, and/or resists dislocation from its implantation site.

SUMMARY

In accordance with an aspect of the present disclosure, a driving instrument for adjusting a spinal implant includes an outer shaft and an inner shaft. The outer shaft includes a distal end configured to actuate a proximal adjustment assembly of a spinal implant, and the inner shaft includes a distal end configured to actuate a distal adjustment assembly of the spinal implant. The inner shaft is disposed within the outer shaft, with a proximal end of the inner shaft extending proximally from the outer shaft. The proximal end is configured to be rotated such that rotation of the inner shaft results in simultaneous rotation of the inner and outer shafts, with rotation of the outer shaft ceasing at a first value of resistance associated with the proximal adjustment assembly and rotation of the inner shaft ceasing at a second value of resistance associated with the distal adjustment assembly such that cessation of rotation of the inner shaft is independent from cessation of rotation of the outer shaft.

In accordance with another aspect of the present disclosure, a system for implanting a spinal implant into a disc space between adjacent vertebral bodies includes a spinal implant and a driving instrument. The spinal implant includes proximal and distal adjustment assemblies that are independently operable to change a height of the proximal or distal region, respectively, of the spinal implant. The driving instrument includes an outer shaft and an inner shaft. The outer shaft includes a distal end configured to actuate the proximal adjustment assembly of the spinal implant, and the inner shaft includes a distal end configured to actuate the distal adjustment assembly of the spinal implant. The inner shaft is disposed within the outer shaft, with a proximal end of the inner shaft extending proximally from the outer shaft. The proximal end is configured to be rotated such that rotation of the inner shaft results in simultaneous rotation of the inner and outer shafts to actuate both the proximal and distal adjustment assemblies, with rotation of the outer shaft ceasing at a first value of resistance associated with the proximal adjustment assembly and rotation of the inner shaft ceasing at a second value of resistance associated with the distal adjustment assembly such that cessation of rotation of the inner shaft is independent from cessation of rotation of the outer shaft.

In accordance with yet another aspect of the present disclosure, a method of implanting a spinal implant into a disc space between adjacent vertebral bodies includes: inserting a driving instrument into engagement with a spinal implant disposed within a disc space, the driving instrument including: an outer shaft including a distal end configured to actuate a proximal adjustment assembly of a spinal implant; and an inner shaft disposed within the outer shaft, the inner shaft including a distal end configured to actuate a distal adjustment assembly of the spinal implant and a proximal extending proximally from the outer shaft; and rotating the inner shaft of the driving instrument to simultaneously rotate both the inner and outer shafts to actuate both the proximal and distal adjustment assemblies.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 6A is a perspective view of the system of FIG. 4, with the insertion instrument in the open position and the spinal implant aligned with the insertion instrument;

FIG. 6B is a close-up view of the area of detail indicated in FIG. 6A;

FIG. 7A is a perspective view of the system of FIG. 4, with the insertion instrument in a closed position and the spinal implant releasably secured to the insertion instrument;

FIG. 7B is a close-up view of the area of detail indicated in FIG. 7A;

FIG. 10 is a perspective view of a system including the spinal implant of FIG. 1 and a driving instrument in accordance with an embodiment of the present disclosure;

FIG. 14A is a side view of the driving instrument of FIG. 10, in a lordosis adjusting position;

FIG. 14B is a cross-sectional view of the driving instrument of FIG. 14A, taken along section line 14B-14B of FIG. 14A;

FIG. 21A is a side view of the driving instrument of FIG. 19;

FIG. 21B is a cross-sectional view of the driving instrument of FIG. 21A, taken along section line 21B-21B of FIG. 21A;

FIG. 23A is a side view of a sleeve in accordance with an embodiment of the present disclosure;

FIG. 23B is a top view of the sleeve of FIG. 23A;

FIG. 23C is an end view of the sleeve of FIG. 23A;

DETAILED DESCRIPTION

Figure 2:
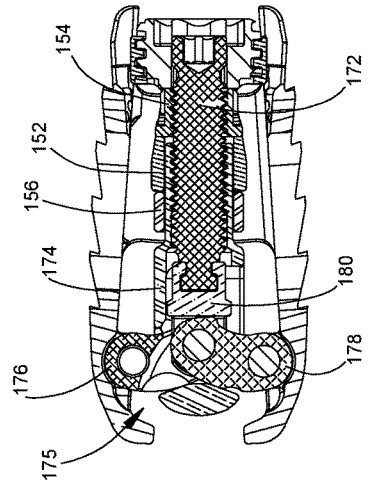
FIG. 2 is a side cross-sectional view of the spinal implant and the set screw of FIG. 1.

Embodiments of the present disclosure are now described in detail with reference to the drawings in which like reference numerals designate identical or corresponding elements in each of the several views. The term "clinician" refers to a doctor (e.g., a surgeon), a nurse, or any other care provider, and may include support personnel. Throughout this description, the term "proximal" refers to a portion of a system, device, or component thereof that is closer to a clinician, and the term "distal" refers to the portion of the system, device, or component thereof that is farther from the clinician.

Figure 1:
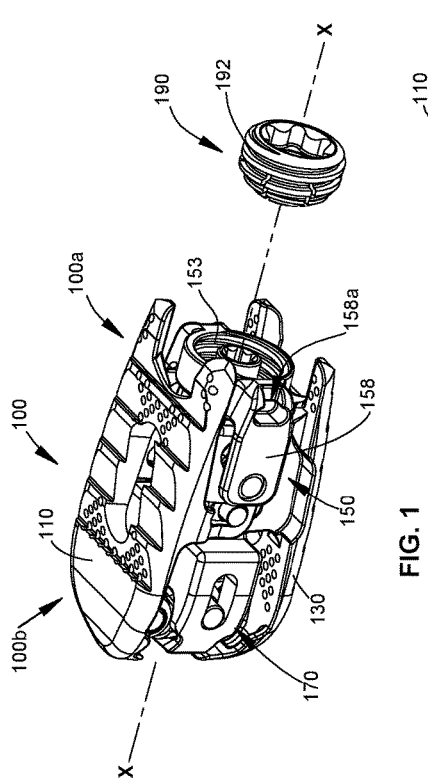
FIG. 1 is a perspective view, with parts separated, of a spinal implant and a set screw in accordance with an embodiment of the present disclosure.

Referring now to the drawings, FIG. 1 illustrates an embodiment of an expandable spinal implant or a spinal implant 100 for use in a system of the present disclosure. Spinal implant 100 has a proximal region 100a and a distal region 100b extending along a longitudinal axis "X." The spinal implant 100 includes an upper body 110 and a lower body 130 disposed in opposed relation relative to each other and coupled together by a proximal adjustment assembly 150 and a distal adjustment assembly 170. The proximal and distal adjustment assemblies 150, 170 are independently operable or movable to allow for adjustment in the angular relationship and vertical distance between the upper and lower bodies 110, 130 of the proximal and/or distal regions 100a, 100b of the spinal implant 100 to achieve a desired configuration of the spinal implant 100.

The spinal implant 100 is movable between a collapsed configuration (e.g., a minimum distance at which the upper and lower bodies 110, 130 may be positioned relative to each other) and a fully expanded configuration (e.g., a maximum distance at which the upper and lower bodies 110, 130 may be positioned relative to each other), and includes a number of partially expanded configurations. The desired configuration of the spinal implant 100 may be locked in place via a set screw 190 that is engageable with the proximal and distal adjustment assemblies 150, 170.

Figure 3:
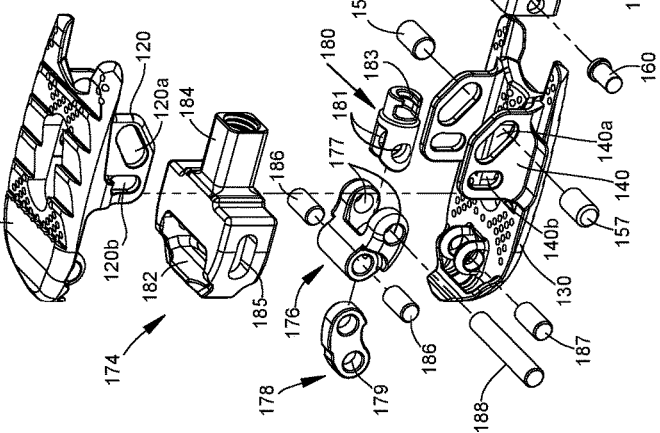
FIG. 3 is an exploded view of the spinal implant of FIG. 1.

As shown in FIGS. 2 and 3, in conjunction with FIG. 1, the proximal adjustment assembly 150 includes a linkage body 152, a drive nut or flange nut 154 positionable within the linkage body 152, and a coupler 156 disposed distally of the linkage body 152. The linkage body 152 and the coupler 156 are sized and shaped to engage, and be supported on, a shaft 184 of an expander 174 of the distal adjustment assembly 170. The linkage body 152 includes a threaded inner surface 153 configured to mate with a threaded outer surface 192 of the set screw 190, and a pair of arms 158 extending along lateral sides of the linkage body 152. The pair of arms 158 includes proximal cavities 158a that are dimensioned to engage an insertion instrument 200 (see e.g. FIG. 4) and distal holes 158b that are aligned with, and coupled to, angled slots 120a, 140a of proximal fins 120, 140 of the upper and lower bodies 110, 130 via a first set of pins 157 to adjustably couple the upper and lower bodies 110, 130 together. The coupler 156 includes nubs 160 extending laterally therefrom that are aligned with, and coupled to, vertical slots 120b, 140b of the proximal fins 120, 140 of the upper and lower bodies 110, 130.

The flange nut 154 has a threaded opening 163 defined therethrough that is configured to threadably engage a drive screw or threaded post 172 of the distal adjustment assembly 170, and a shaped outer surface 165 configured to mate with a driving instrument 300, 400 (see e.g., FIGS. 10 and 19, respectively) such that either the flange nut 154 or the threaded post 172 may be rotated and axially translated with respect to the other. The flange nut 154 includes a distal flange 166 dimensioned to be received within the linkage body 152 such that movement of the flange nut 154 results in movement of the linkage body 152.

Accordingly, movement of the flange nut 154 distally moves the linkage body 152 distally causing the first set of pins 157 to translate within the angled slots 120a, 140a of the proximal fins 120, 140 and the nubs 160 of the coupler 156 to translate within the vertical slots 120b, 140b of the proximal fins 120, 140 to increase the distance between the upper and lower bodies 110 and 130 in the proximal region 100a of the spinal implant 100. Conversely, movement of the flange nut 154 proximally moves the linkage body 152 proximally to reduce the distance between the upper and lower bodies 110, 130 in the proximal region 100a of the spinal implant 100.

With continued reference to FIGS. 1-3, the distal adjustment assembly 170 includes the threaded post 172, the expander 174, and a pivot linkage assembly 175 including an upper pivot linkage 176, a lower pivot linkage 178, and a connector linkage 180. The threaded post 172 includes an elongated threaded body 172a having a recessed proximal end 172b configured to mate with a driving instrument 300, 400 (see e.g., FIGS. 10 and 19, respectively) and a distal end 172c disposed within a recess 183 of the connector linkage 180. The recessed proximal end 172b may have a hex feature, e.g., hexagonal or hexolobular in shape, or any other suitable configuration that is engageable with a suitable driving instrument to enable the driving instrument to control the insertion and/or advancement, as well as retraction and/or withdrawal, of the threaded post 172 within the spinal implant 100.

The upper pivot linkage 176 is pivotably coupled to the upper body 110 (e.g., about a second set of pins 186), and the lower pivot linkage 178 is pivotably coupled to the lower body 130 (e.g., about a pin 187). Holes 177, 179, 181 of the upper pivot linkage 176, the lower pivot linkage 178, and the connector linkage 180, respectively, are aligned with each other and with longitudinal slots 185 defined in the expander 174, and a pin 188 is disposed therethrough for pivotably securing the upper and lower bodies 110 and 130 to the expander 174 of the distal adjustment assembly 170 via the pivot linkage assembly 175.

Accordingly, rotation of the threaded post 172 in a first direction advances the threaded post 172 distally through the flange nut 154 and the shaft 184 of the expander 174 which, in turn, pushes the connector linkage 180 distally and drives the upper and lower pivot linkages 176, 178 against a double ramped inner surface 182 of the expander 174 thereby increasing the height between the upper and lower bodies 110, 130 at the distal region 100b of the spinal implant 100. Rotation of the threaded post 172 in a second, reverse direction moves the threaded post 172 proximally which, in turn, moves the connector linkage 180 proximally to allow the upper and lower pivot linkages 176, 178 to collapse, thereby decreasing the height between the upper and lower bodies 110, 130 at the distal region 100b of the spinal implant 100.

For a detailed description of the structure and function of exemplary spinal implants suitable for use in a system of the present disclosure, reference may be made to commonly owned U.S. patent application Ser. No. 15/657,796, filed Jul. 24, 2017, and U.S. Patent Appl. Pub. No. 2016/0166396, each entitled "Expandable Spinal Implants," the entire contents of each of which are incorporated herein by reference.

Figure 4:
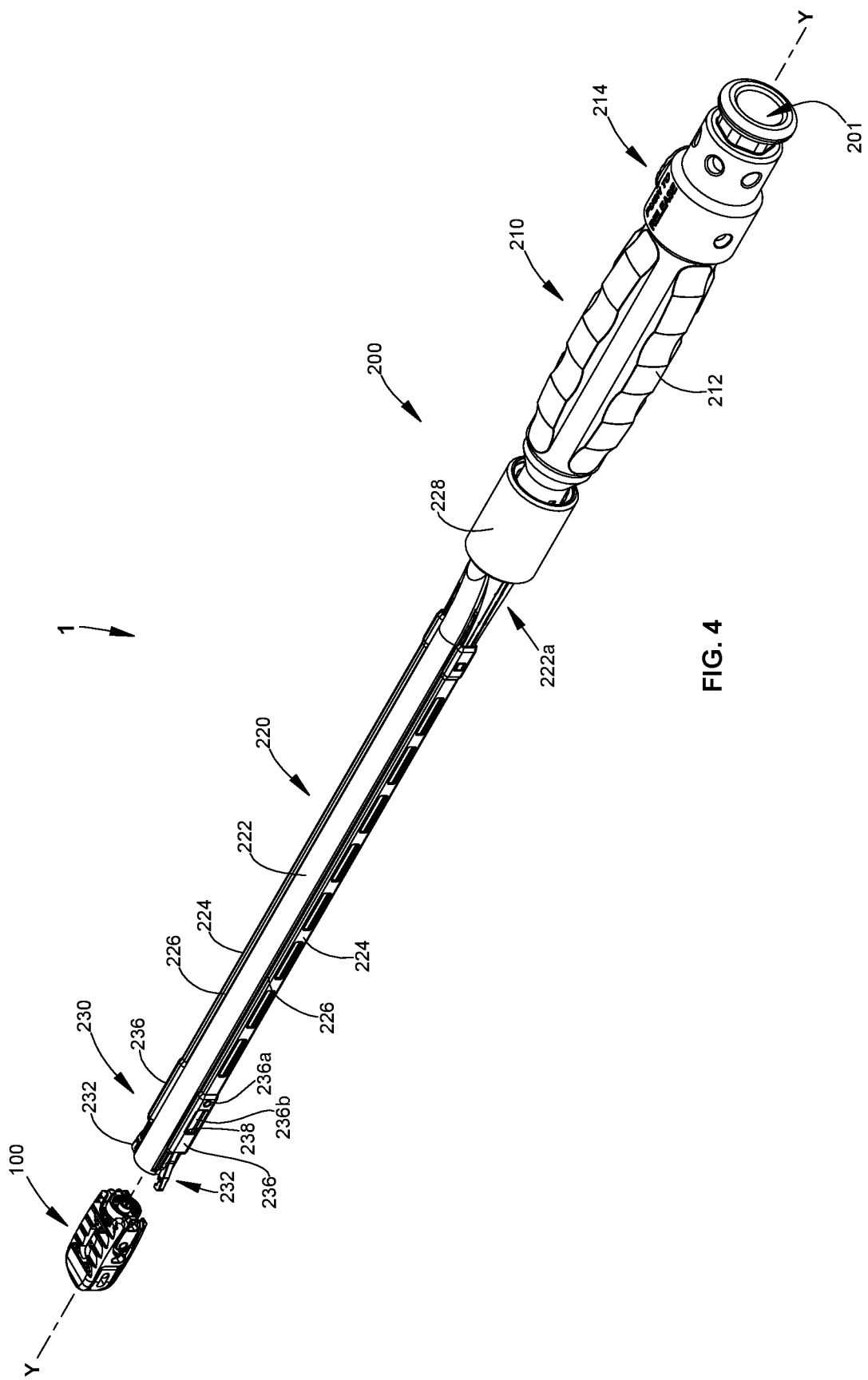
FIG. 4 is a perspective view of a system including the spinal implant of FIG. 1 and an insertion instrument in an open configuration, in accordance with an embodiment of the present disclosure.
Figure 5A:
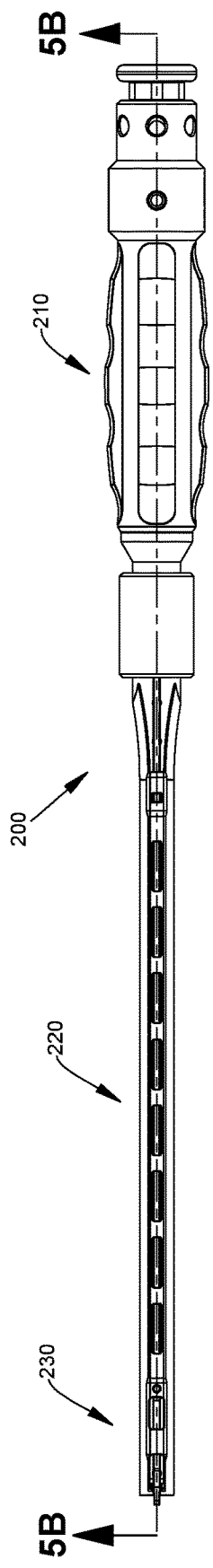
FIG. 5A is a side view of the insertion instrument of FIG. 4.
Figure 5B:
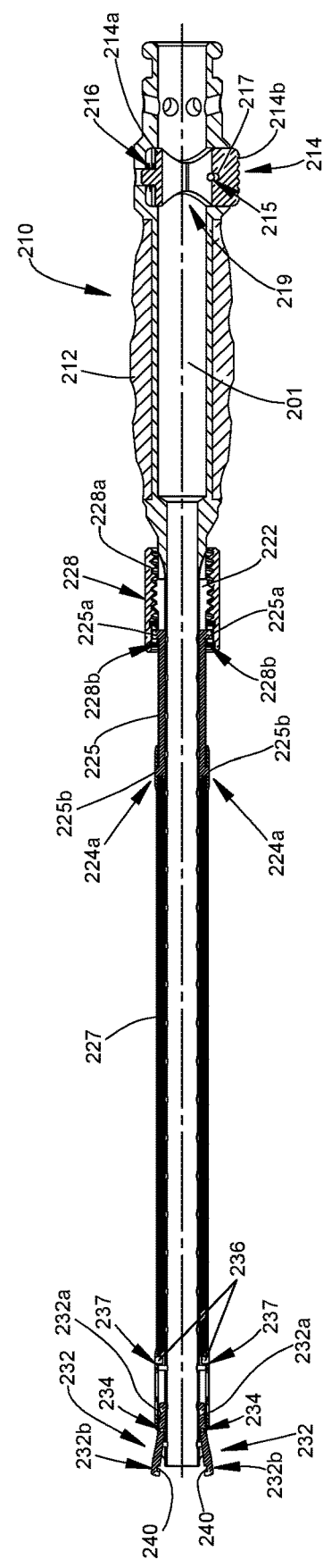
FIG. 5B is a cross-sectional view of the insertion instrument of FIG. 5A, taken along section line 5B-5B of FIG. 5A.

With reference now to FIGS. 4-5B, a system 1 including an insertion instrument 200 for inserting and/or positioning the spinal implant 100 into an intervertebral disc space is shown. The insertion instrument 200 includes, from proximal to distal, a handle 210, a body portion 220, and a connector assembly 230 extending along a longitudinal axis "Y" that is coincident with the longitudinal axis "X" (FIG. 1) of the spinal implant 100. A lumen 201 is defined through the insertion instrument 200 (i.e., the handle 210, the body portion 220, and the connector assembly 230) and configured to receive a tool (see e.g., the insertion shaft 250 of FIG. 8 or the driving instruments 300, 400 of FIGS. 10 and 19, respectively), as described in detail below.

The handle 210 of the insertion instrument 200 includes a grip portion 212 and a button 214. The button 214 includes a body 214a disposed within the handle 210 and a pad 214b extending laterally through the handle 210. A pin 215 is secured to the handle 210 and extends into an elongated hole 217 of the button 214 such that the button 214 is movable relative to the handle 210. The button 214 is biased towards a first position by a spring 216 (e.g., a wave spring) disposed within the handle 210 such that a slot 219 defined through the body portion 214a of the button 214 is axially misaligned with the lumen 201 to retain a tool (not shown) therein. The button 214 is depressible into a second position that aligns the slot 219 with the lumen 201 to facilitate removal of a tool therefrom.

The body portion 220 includes an elongated shaft 222, elongated rails 224 slidably movable along tracks 226 disposed on opposed sides of the elongated shaft 222, and a rotation knob 228 disposed about a proximal portion 222a of the elongated shaft 222. The rotation knob 228 includes a threaded inner surface 228a that is threadably engaged with the proximal portion 222a of the elongated shaft 222, and a distal recess 228b defined in the inner surface 228a that is configured to receive a proximal flange 225a of a proximal rod 225 configured to move the elongated rails 224 longitudinally. A distal flange 225b of the proximal rod 225 is engaged with a proximal holes 224a defined in the elongated rails 224. A distal rod 227 is disposed within the tracks 226, adjacent to, and longitudinally aligned with the proximal rod 225, and extends distally towards cover plates 236 of the elongated rails 224.

The connector assembly 230 includes connector arms 232 pivotally secured to opposed sides of the elongated shaft 222 of the body portion 220 via pivot pins 234. The cover plates 236 of the elongated rails 224 are slidably disposed over the connector arms 232. Each of the connector arms 232 includes a proximal portion 232a and a distal portion 232b that are disposed at angles with respect to the longitudinal axis "Y" of the insertion instrument 200. The proximal portion 232a of each connector arm 232 includes a protrusion 238 on an outer surface thereof, and the distal portion 232b of each connector arm 232 includes an engagement feature 240 (e.g., a hook) on an inner surface thereof.

The cover plates 236 each include a u-shaped body configured to engage and ride longitudinally along the tracks 226 of the elongated shaft 222. Each of the cover plates 236 includes a proximal hole 236a engaged with a pin 237 disposed distal to the distal rod 227, and a distal opening 236b configured to receive the respective protrusion 238 of the connector arms 232 when the connector arms 232 are disposed in a closed or grasping position.

As shown in FIGS. 6A and 6B, when the rotation knob 228 of the insertion instrument 200 is disposed in a proximal position, the elongated rails 224 are also disposed in a proximal position. In the proximal position, the cover plates 236 are disposed over the proximal portions 232a of the connector arms 232 such that the proximal portions 232a are substantially aligned with the longitudinal axis "Y" of the insertion instrument 200, and the distal portions 232b of the connector arms 232 extend radially outward relative to the longitudinal axis "Y". In the proximal position, the connector arms 232 are in an open position such that the spinal implant 100 may be placed adjacent the connector assembly 230 of the insertion instrument 200, with the proximal cavities 158a of the linkage body 152 of the surgical implant 100 aligned with the engagement features 240 of the insertion instrument 200.

As shown in FIGS. 7A and 7B, the rotation knob 228 of the insertion instrument 200 may be moved to a distal position by rotating the rotation knob 228 in a first direction which causes a corresponding longitudinal movement of the elongated rails 224 along the tracks 226 of the elongated shaft 222. The distal movement of the connector plates 236 over the connector arms 232 causes the connector arms 232 to pivot about the pivot pins 234 (FIG. 5B) such that the distal portions 232b of the connector arms 232 are substantially aligned/parallel with the longitudinal axis "Y" of the insertion instrument 200 and the proximal portions 232a of the connector arms 232 extend radially outwardly such that the protrusions 238 are deflected into the distal openings 236b of the connector plates 236. In the distal position, the connector arms 232 are in a closed or grasping position and the engagement features 240 of the insertion instrument 200 are engaged with the proximal cavities 158a of the spinal implant 100 thereby releasably securing the insertion instrument 200 to the spinal implant 100.

Figure 8:
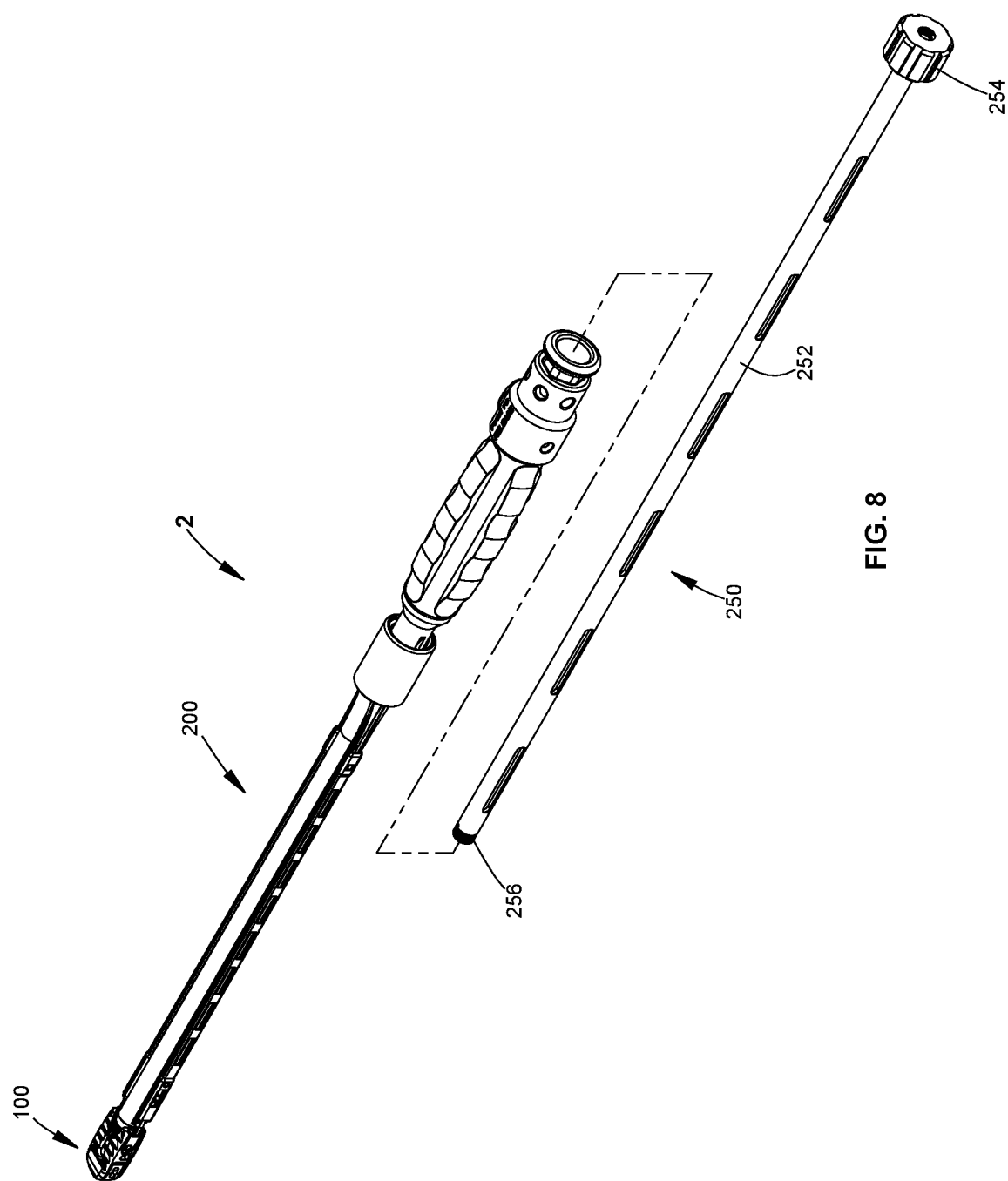
FIG. 8 is a perspective view of a system including the spinal implant and the insertion instrument of FIG. 4, and an insertion shaft in accordance with an embodiment of the present disclosure.

With reference now to FIG. 8, a system 2 includes an insertion shaft 250 positionable within the insertion instrument 200 to aid in aligning and securing the spinal implant 100 to the insertion instrument 200 during insertion and/or positioning of the spinal implant 100 into an intervertebral disc space. The insertion shaft 250 includes an elongate body 252 having a head 254 disposed at a proximal end thereof and a threaded tail 256 disposed at a distal end thereof.

Figure 9A:
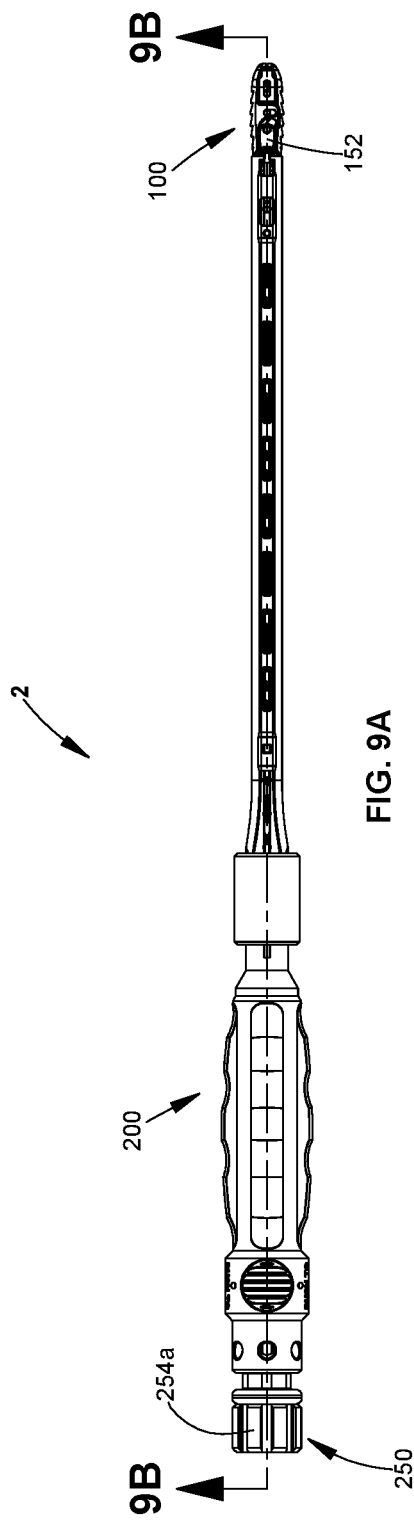
FIG. 9A is a side view of the system of FIG. 8.
Figure 9B:
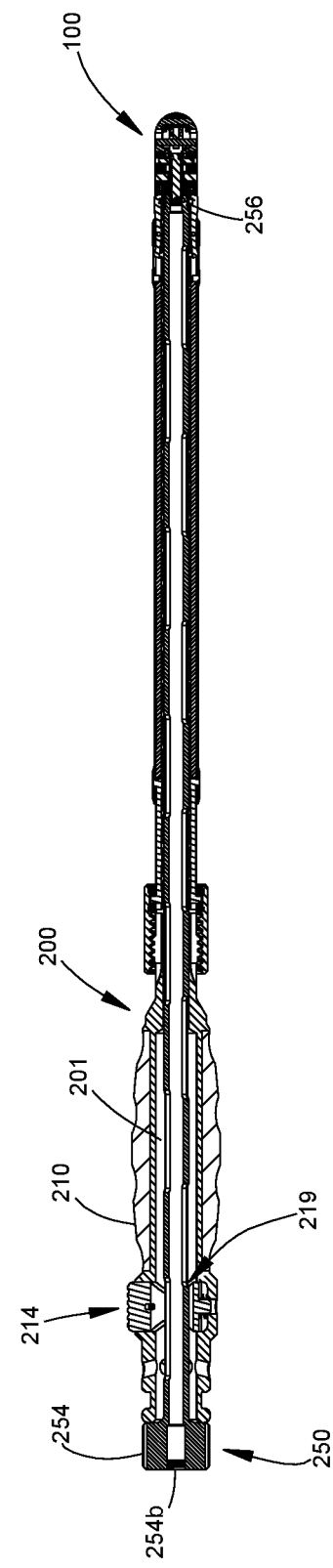
FIG. 9B is a cross-sectional view of the system of FIG. 9A, taken along section line 9B-9B of FIG. 9A.

As shown in FIGS. 9A and 9B, the insertion shaft 250 is inserted into the lumen 201 of the insertion instrument 200 such that the threaded tail 256 is engaged with the threaded inner surface 153 (FIG. 1) of the linkage body 152 of the spinal implant 100 and the head 254 abuts a proximal end of the handle 210. The head 254 includes a grooved outer surface 254a and a partially threaded inner surface 254b. The grooved outer surface 254a is engageable with a tool (not shown) configured to rotate the insertion shaft 250 and the partially threaded inner surface 254b is engageable with a driver (not shown) insertable through the insertion shaft 250.

With the insertion shaft 250 disposed within the insertion instrument 200, the slot 219 of the button 214 is out of alignment with the lumen 201 of the insertion instrument 200 to hold the insertion shaft 250 therein. To release the insertion shaft 250 from the insertion instrument 200, the button 214 is pushed into the handle 210 to align the slot 219 of the button 214 with the lumen 201.

Figure 11:
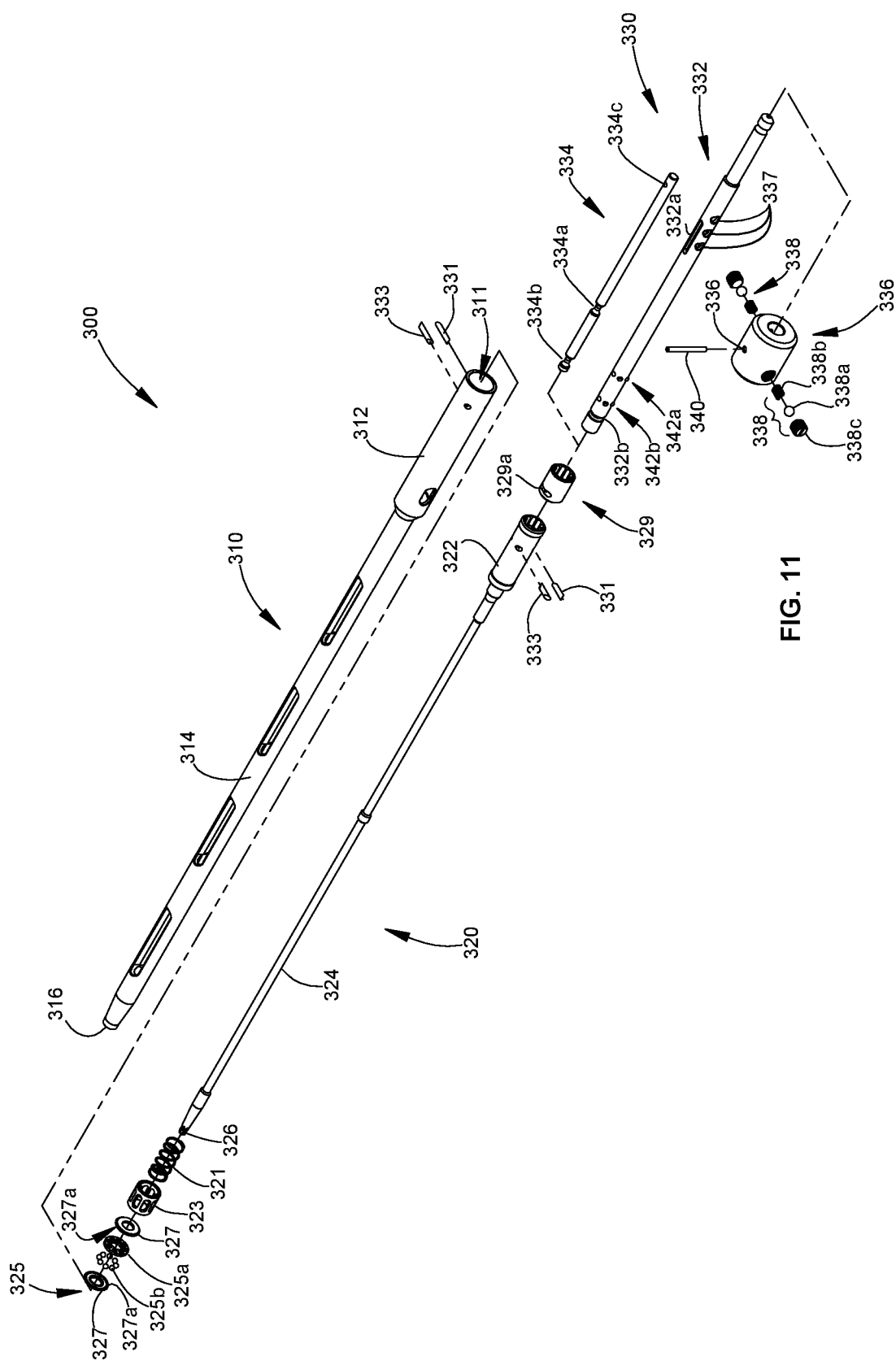
FIG. 11 is an exploded view of the driving instrument of FIG. 10.

Turning now to FIGS. 10 and 11, a system 3 including a driving instrument 300 for driving the expansion and/or contraction of the spinal implant 100 is shown. The driving instrument 300 includes an outer shaft 310, a distal inner shaft 320, and a proximal shaft assembly 330. The outer shaft 310 defines a lumen 311 therethrough, and includes a proximal base portion 312 and an elongated body portion 314 terminating at an open tip 316. The open tip 316 includes an inner surface 316a (see e.g., FIG. 12B) that is complementary in shape with the shaped outer surface 165 (see e.g., FIG. 2) of the flange nut 154 of the spinal implant 100 to engage the flange nut 154.

The distal inner shaft 320 includes a proximal base portion 322 and an elongated body portion 324 terminating at a distal tip 326. The proximal base portion 322 is disposed within the proximal base portion 312 of the outer shaft 310, and the elongated body 324 is disposed within the elongated body portion 314 of the outer shaft 310. The distal tip 326 is a male connector having a complementary geometry to the recessed proximal end 172b (see e.g., FIG. 2) of the threaded post 172 (e.g., a hex feature) of the spinal implant 100 such that the distal tip 326 is receivable therein and configured to engage the threaded post 172.

A spring 321 and a bushing 323 are inserted over the distal inner shaft 320, distal to the proximal base portion 322 of the distal inner shaft 320 and within a distal portion of the proximal base portion 312 of the outer shaft 310. The spring 321 is at least partially retained within the bushing 323. A bearing assembly 325 is also inserted over the distal inner shaft 320. The bearing assembly 325 includes a bearing retainer 325a having a ball bearings 325b positioned therein, and end plates 327 positioned on opposing sides of the bearing retainer 325*a*. The end plates 327 each include an annular grooved surface 327*a* facing the bearing retainer 325*a* thereby providing a track to support and maintain the position of the ball bearings 325*b* such that the ball bearings 325*b* run smoothly therebetween and freely within the bearing retainer 325*a*.

A connector 329 is also disposed within the proximal base portion 312 of the outer shaft 310, proximal to the proximal base portion 322 of the distal inner shaft 320. The connector 329 includes pockets 329*a* defined therethrough, as described in further detail below.

The proximal shaft assembly 330 includes a proximal outer shaft 332, a proximal inner shaft 334, and an adjustment knob 336. The proximal outer shaft 332 is configured to be slidably disposed within the connector 329 and the proximal base portion 322 of the distal inner shaft 320, which are each disposed within the outer shaft 310, as described above. A first set of pins 331 is inserted through the proximal base portion 322 of the distal inner shaft 320 along a distal groove 332*b* defined around the proximal outer shaft 332, and a second set of pins 333 is inserted through the proximal base portion 312 of the outer shaft 310 and the connector 329.

The proximal outer shaft 332 includes proximal and distal ball bearing assemblies 342*a*, 342*b* disposed therein. The proximal inner shaft 334 is slidably disposed within the proximal outer shaft 332, retaining the proximal and distal ball bearing assemblies 342*a*, 342*b* therebetween. The adjustment knob 336 is slidably disposed over the proximal outer shaft 332. Plunger assemblies 338 are positioned in lateral side openings 336*a* of the adjustment knob 336. Each plunger assembly 338 includes a ball 338*a*, a spring 338*b*, and a screw 338*c* retaining the ball and spring 338*a*, 338*b* within the adjustment knob 336 adjacent to the proximal outer shaft 332. The balls 338 are configured to engage recesses 337 defined in the proximal outer shaft 332 upon actuation of the adjustment knob 336 between a height adjusting position "H" (FIGS. 12A and 12B), a posterior or proximal adjusting position "P" (FIGS. 13A and 13B), and a lordosis, anterior, or distal adjusting position "L" (FIGS. 14A and 14B). A pin 340 extends through opposed openings 336*b* of the adjustment knob 336, a longitudinal opening 332*a* defined in the proximal outer shaft 332, and an opening 334*c* defined through the proximal inner shaft 334. Accordingly, the adjustment knob 336 may be slid between the height adjusting position "H" (FIGS. 12A and 12B), the proximal adjusting position "P" (FIGS. 13A and 13B), and the distal adjusting position "L" (FIGS. 14A and 14B) relative to the proximal outer shaft 332 which, in turn, causes a corresponding longitudinal movement of the proximal inner shaft 334.

Proximal and distal recessed grooves 334*a*, 334*b* defined around the proximal inner shaft 332 and the pockets 329*a* of the connector 329 are configured to engage/disengage the proximal and/or distal ball bearing assemblies 342*a*, 342*b* disposed within the proximal outer shaft 332 during actuation of the adjustment knob 336 between the height, proximal, and distal adjusting positions to effect the function of the driving instrument 300. Specifically, the proximal and distal ball bearing assemblies 324*a*, 342*b* are configured to float above or below the proximal outer shaft 332 to actively engage or disengage the distal inner shaft 320 and/or the outer shaft 310.

Figure 12A:
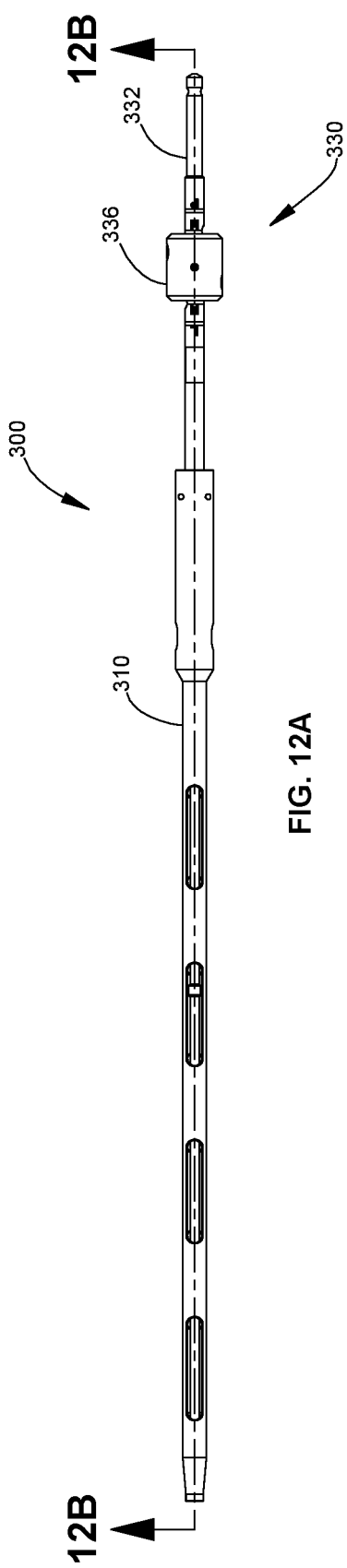
FIG. 12A is a side view of the driving instrument of FIG. 10, in a height adjusting position.
Figure 12B:
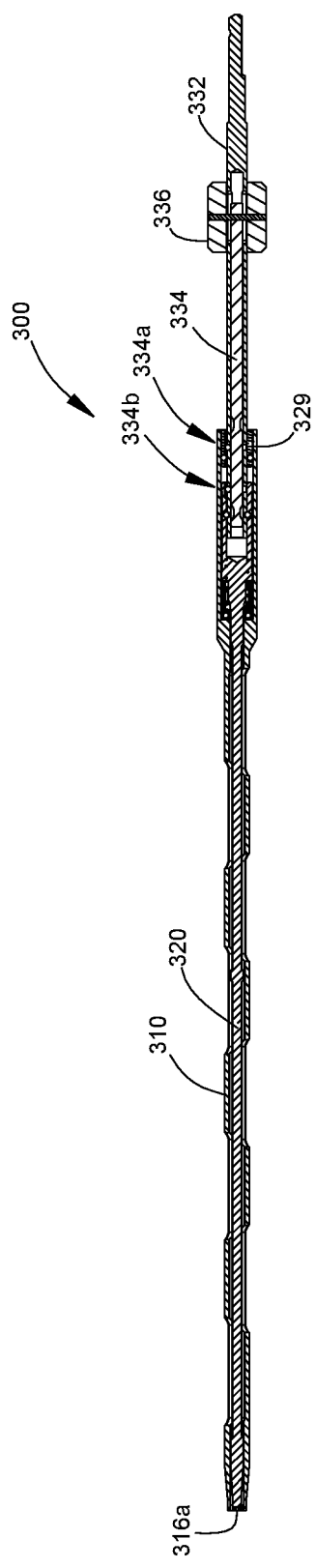
FIG. 12B is a cross-sectional view of the driving instrument of FIG. 12A, taken along section line 12B-12B of FIG. 12A.

As shown in FIGS. 12A and 12B, when the adjustment knob 336 is in the height adjusting position "H", the proximal and distal ball bearing assemblies 342*a*, 342*b* are disengaged from the proximal and distal recessed grooves 334*a*, 334*b* (FIG. 11) of the proximal inner shaft 334, as well as the pockets 329*a* (FIG. 11) of the connector 329. Accordingly, actuation of the proximal outer shaft 332 of the proximal adjustment assembly 330 allows both the outer shaft 310 and the distal inner shaft 320 to be actuated such that the proximal and distal adjustment assemblies 150, 170 (see e.g., FIG. 1) of the spinal implant 100 are simultaneously adjusted.

Figure 13A:
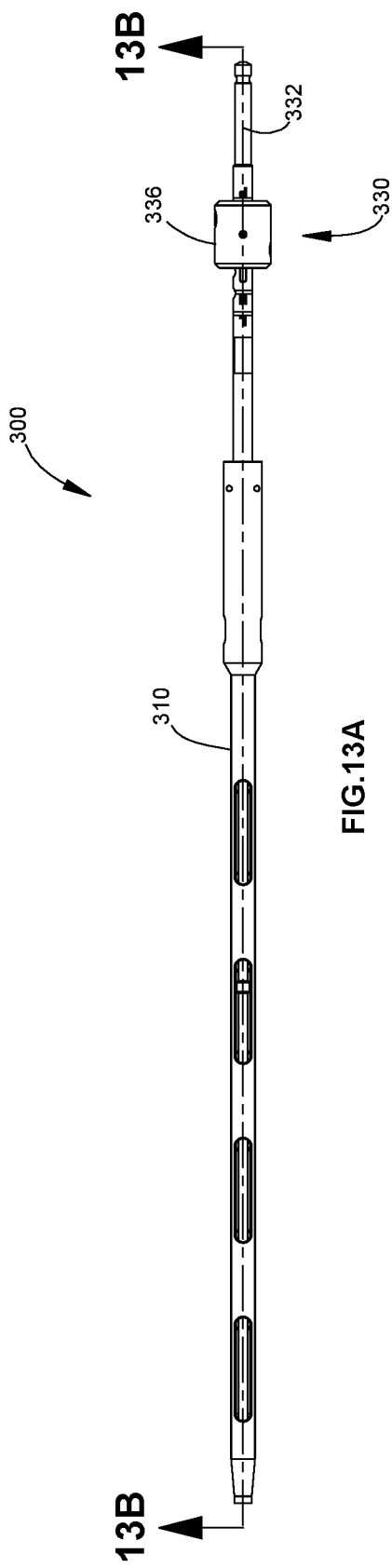
FIG. 13A is a side view of the driving instrument of FIG. 10, in a posterior adjusting position.
Figure 13B:
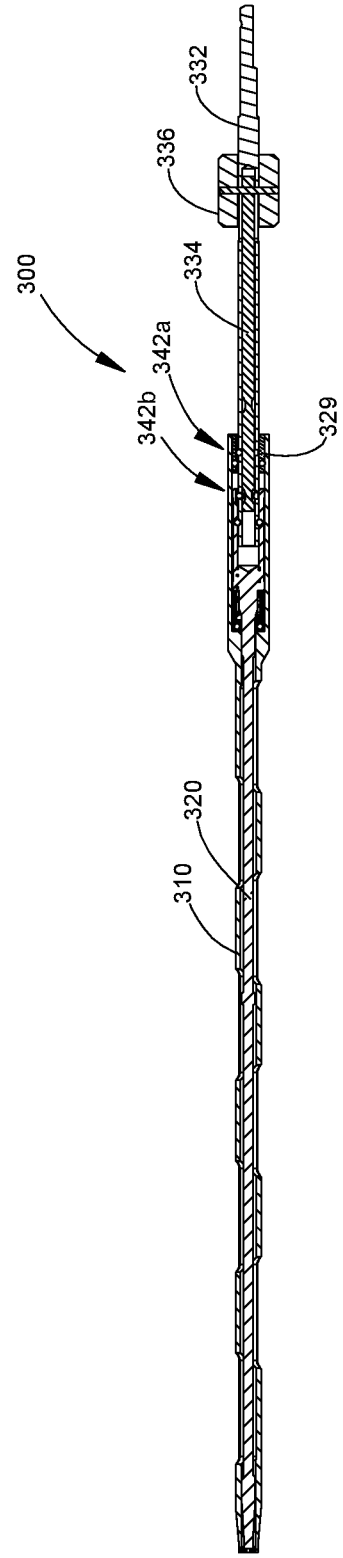
FIG. 13B is a cross-sectional view of the driving instrument of FIG. 13A, taken along section line 13B-13B of FIG. 13A.

When the adjustment knob 336 is moved to the posterior adjusting position "P", as shown in FIGS. 13A and 13B, the proximal inner shaft 334 is slid proximally such that the proximal ball bearing assembly 342*a* is disengaged from the proximal inner shaft 334 and the distal ball bearing assembly 342*b* is engaged with the pocket 329*a* of the connector 329. Accordingly, actuation of the proximal outer shaft 332 of the proximal adjustment assembly 330 causes only the outer shaft 310 to be actuated such that only the proximal region 110*a* of the spinal implant 100 is actuated.

When the adjustment knob 336 is moved to the lordosis adjusting position "L", as shown in FIGS. 14A and 14B, the proximal inner shaft 334 is slid distally such that the proximal ball bear assembly 342*a* is engaged with the proximal recessed groove 334*c* of the proximal inner shaft 334 and the distal ball bearing assembly 342*b* is disengaged from the pockets 329*a* of the connector 329. Accordingly, actuation of the proximal outer shaft 332 of the proximal adjustment assembly 330 causes only the distal inner shaft 320 to be actuated such that only the distal region 110*b* of the spinal implant 100 is actuated.

Figure 15:
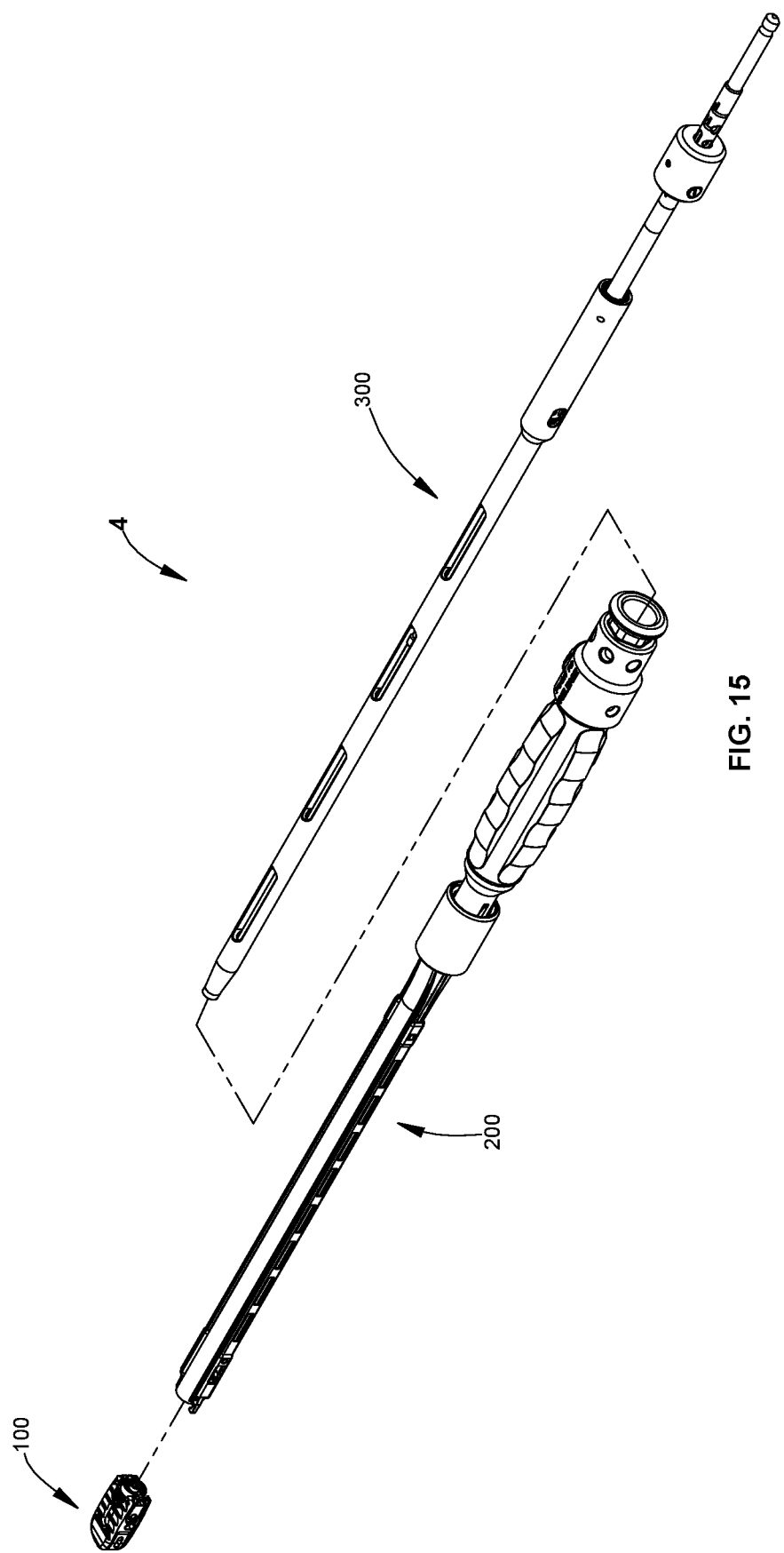
FIG. 15 is a perspective view of a system including the insertion instrument of FIG. 4, the spinal implant of FIG. 1, and the driving instrument of FIG. 10.
Figure 16:
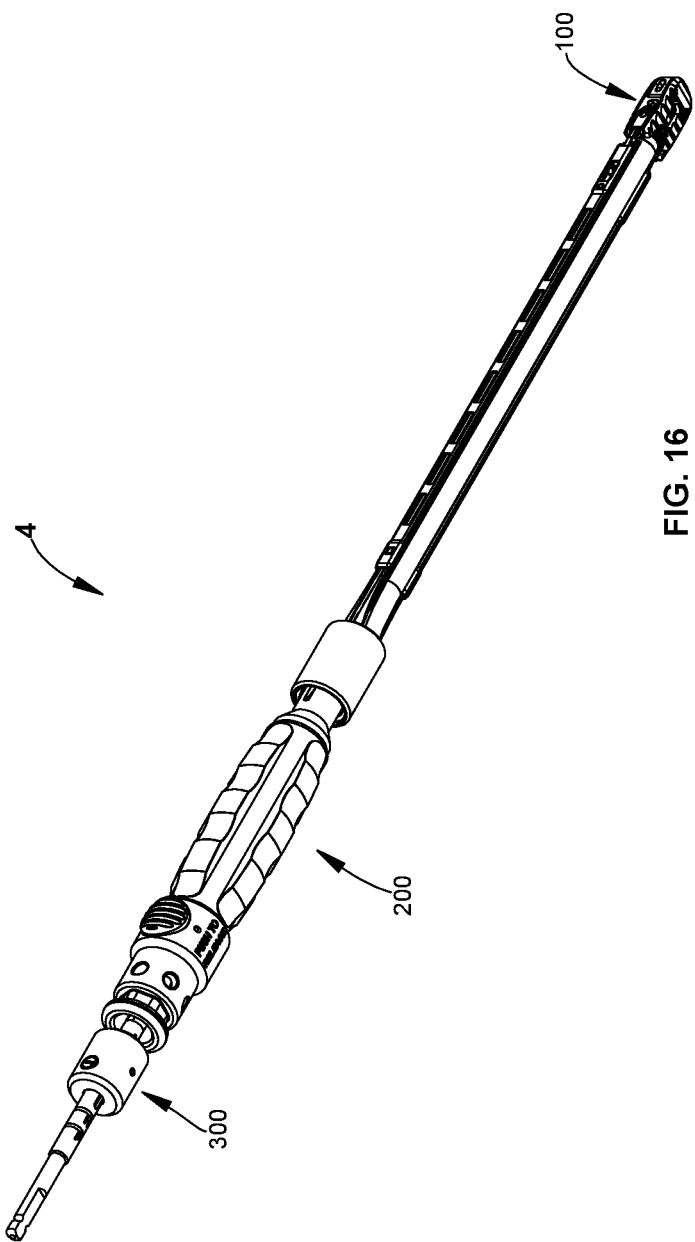
FIG. 16 is a perspective view of the system of FIG. 15.
Figure 17A:
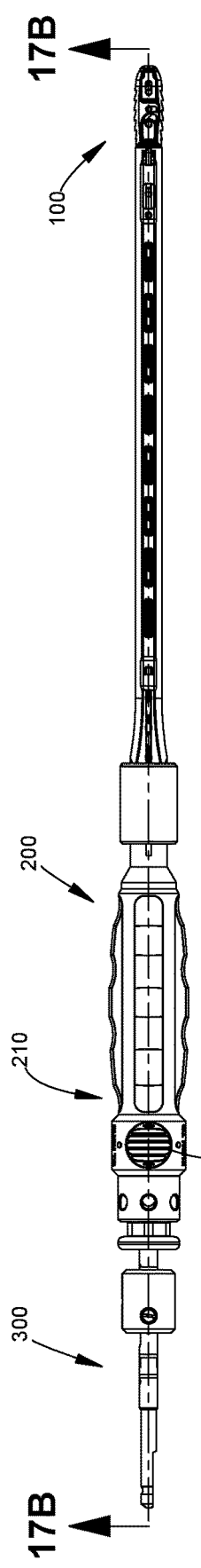
FIG. 17A is a side view of the system of FIG. 16.
Figure 17B:
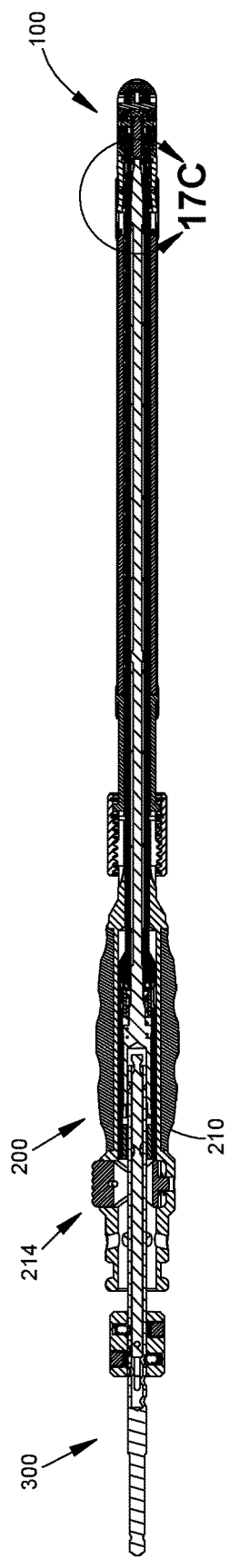
FIG. 17B is a cross-sectional view of the system of FIG. 17A, taken along section line 17B-17B of FIG. 17A.
Figure 17C:
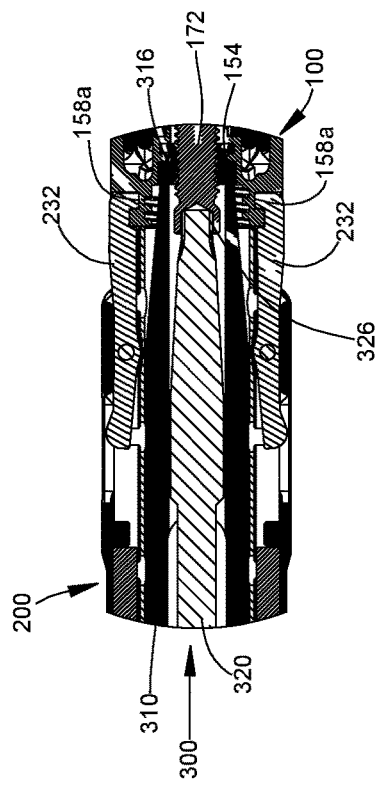
FIG. 17C is a close-up view of the area of detail indicated in FIG. 17B.
Figure 18A:
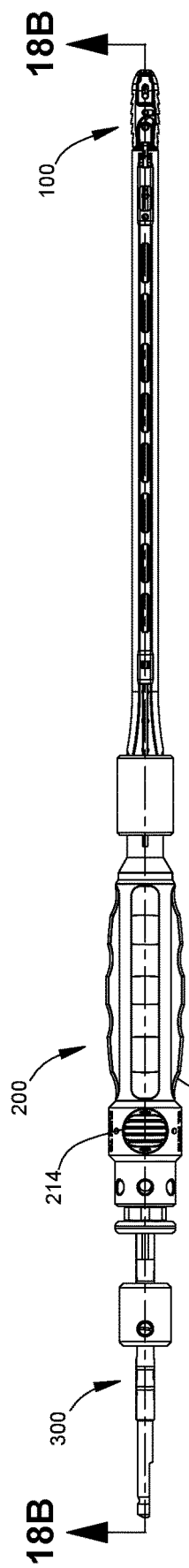
FIG. 18A is a side view of the system of FIG. 16, with a button of the insertion instrument compressed into a handle of the insertion instrument.
Figure 18B:
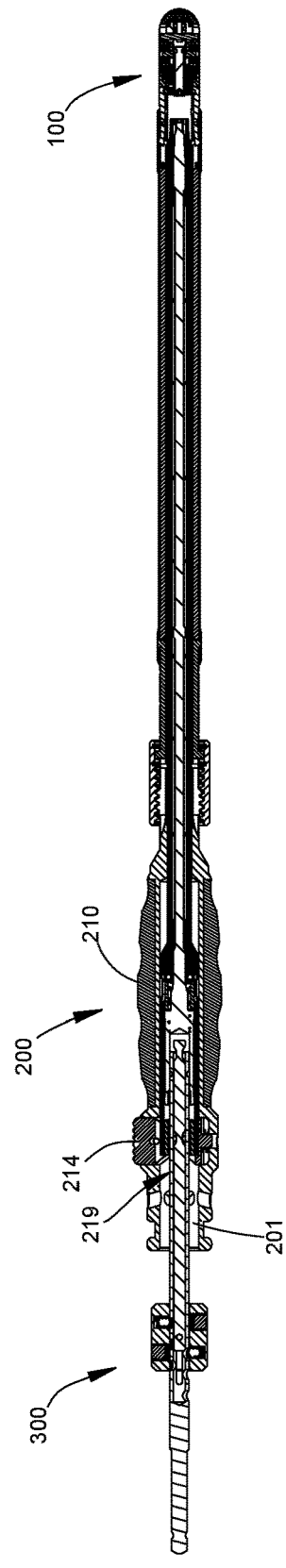
FIG. 18B is a cross-sectional view of the system of FIG. 18A, taken along section line 18B-18B of FIG. 18A.

With reference now to FIGS. 15 and 16, a system 4 includes the driving instrument 300 positionable within the insertion instrument 200 to drive the expansion or contraction of the spinal implant 100. As shown in FIGS. 17A-17C, with the connector arms 232 of the insertion instrument 200 engaged with the proximal cavities 158*a* of the spinal implant 100, the driving instrument 300 is inserted into the insertion instrument 200 such that the open tip 316 and the distal tip 326 of the outer and distal inner shafts 310, 320, respectively, of the driving instrument 300 are engaged with the respective flange nut 154 and threaded post 172 of the spinal implant 100. While the driving instrument 300 is shown in the lordosis adjusting position "L", such that only the distal inner shaft 320 is rotated upon actuation of the driving instrument 300 (e.g., to accommodate for lordosis), it should be understood that the driving instrument 300 may be used in any of the positions described above. After the spinal implant 100 is adjusted to a desired configuration, the driving instrument 300 may be removed from the insertion instrument 200 by pressing the button 214 of the handle 210 of the insertion instrument 200, as shown in FIGS. 18A and 18B, to align the slot 219 of the button 214 with the lumen 201 of the insertion instrument 200, and pulling the driving instrument 300 proximally therefrom.

Figure 19:
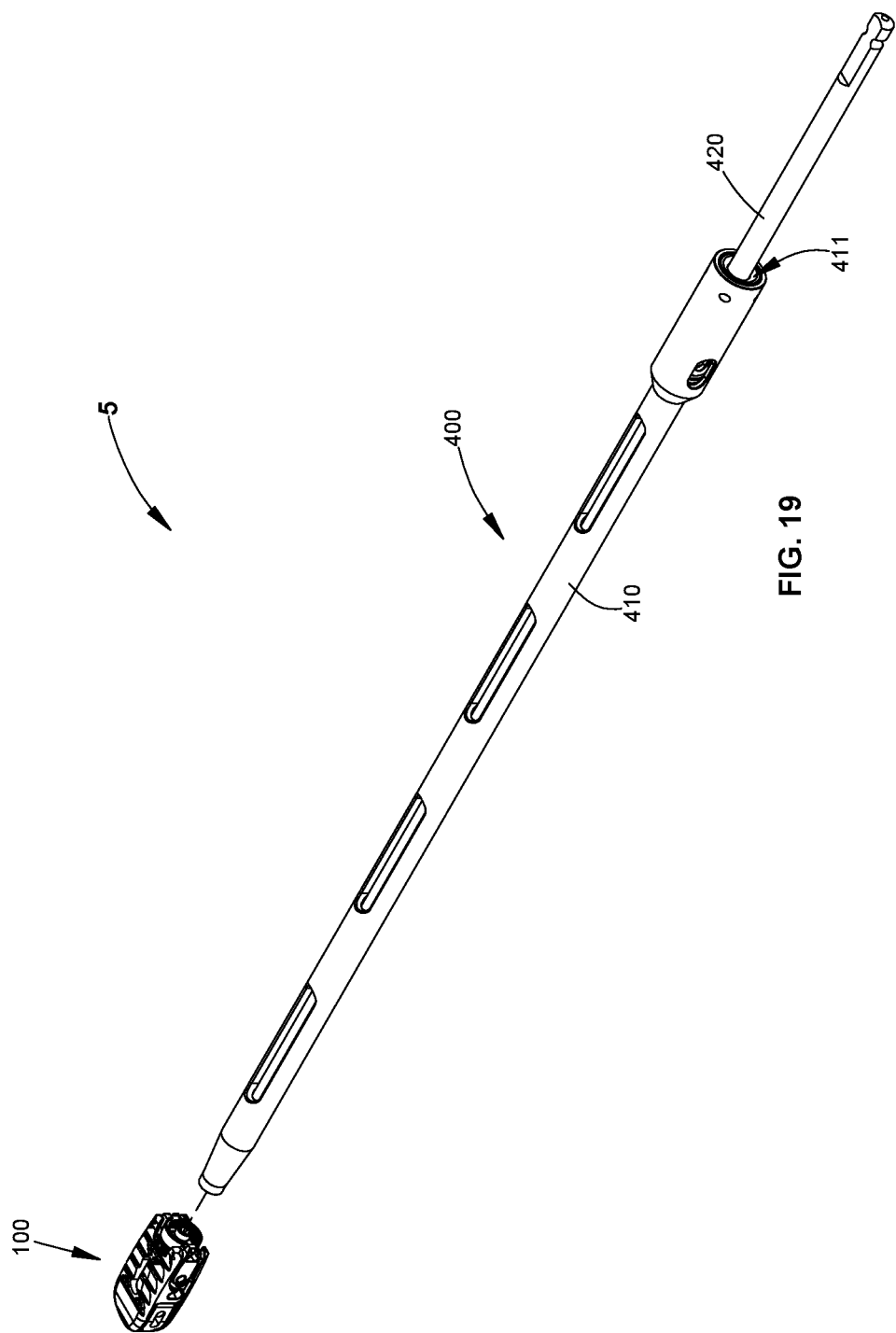
FIG. 19 is a perspective view of a system including the spinal implant of FIG. 1 and a driving instrument in accordance with another embodiment of the present disclosure.
Figure 20:
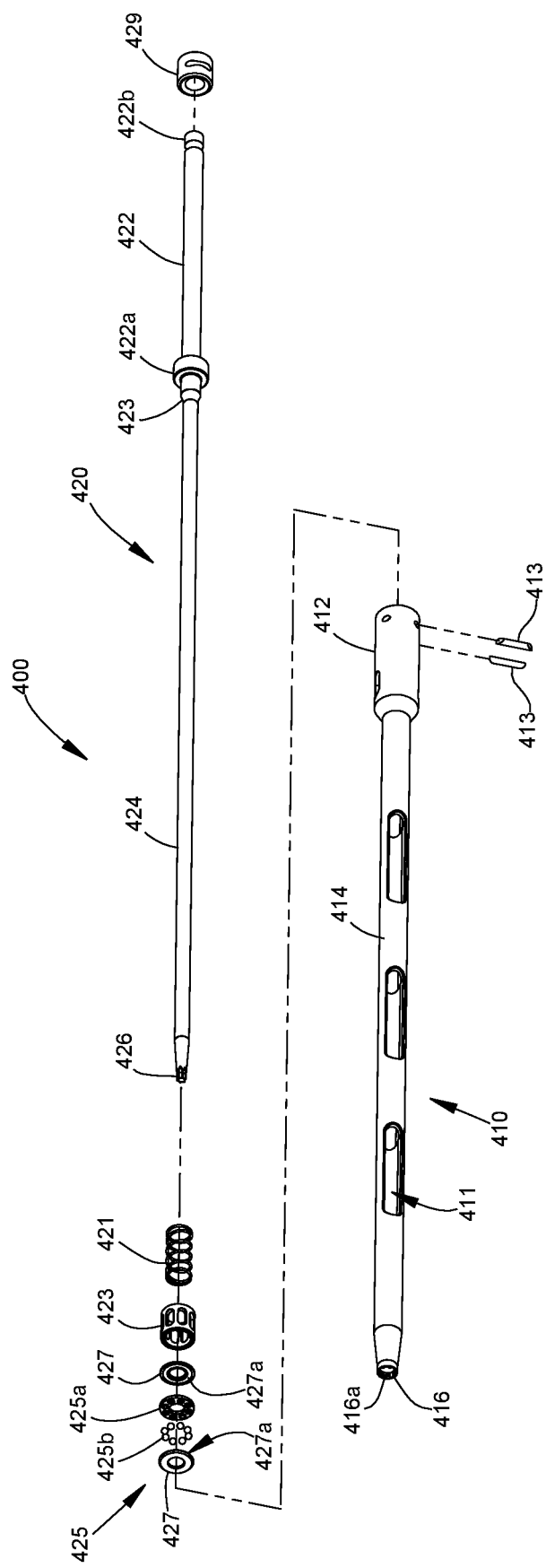
FIG. 20 is an exploded view of the driving instrument of FIG. 19.

Turning now to FIGS. 19 and 20, a system 5 including a driving instrument 400 for driving the expansion and/or contraction of the spinal implant 100 is shown. The driving instrument 400 includes an outer shaft 410 and an inner shaft 420. The outer shaft 410 defines a lumen 411 therethrough, and includes a proximal base portion 412 and an elongated body portion 414 terminating at an open tip 416. The open tip 416 includes an inner surface 416*a* that is complementary in shape with the shaped outer surface 165 (see e.g., FIG. 2) of the flange nut 154 of the spinal implant 100 to engage the flange nut 154.

The inner shaft 420 includes a proximal portion 422, an elongated body portion 424 terminating at a distal tip 426, and a tapered portion 423 interconnecting the proximal and elongated body portions 422, 424. The proximal portion 422 has a collared section 422a having an outer dimension complementary in size and shape with an inner surface of the proximal base portion 412 of the outer shaft 410. The distal tip 426 is a male connector having a complementary geometry to the recessed proximal end 172b (see e.g., FIG. 2) of the threaded post 172 (e.g., a hex feature) such that the distal tip 426 is receivable therein and configured to engage the threaded post 172.

As shown in FIGS. 21A and 21B, in conjunction with FIG. 20, the proximal portion 422 of the inner shaft 420 is disposed within the proximal base portion 412 of the outer shaft 410 and extends proximally therefrom such that a proximal end 422b can be engaged with a tool (not shown) to drive rotation of the driving instrument 400. The elongated body 424 is partially disposed within the proximal base portion 412 of the outer shaft 410 and extends distally within the elongated body portion 414 of the outer shaft 410. A connector 429 is disposed within a proximal portion of the proximal base portion 412 of the outer shaft 410, and is secured therein via pins 413.

A spring 421 and a bushing 423 are inserted over the inner shaft 420, within a distal portion of the proximal base portion 412 of the outer shaft 410. The spring 421 is at least partially retained within the bushing 423. A bearing assembly 425 is also inserted over the inner shaft 420, adjacent to the bushing 423 and within the proximal base portion 412 of the outer shaft 410. The bearing assembly 425 includes a bearing retainer 425a having ball bearings 425b positioned therein, and end plates 427 positioned on opposing sides of the bearing retainer 425a. The end plates 427 each include an annular grooved surface 427a facing the bearing retainer 425a thereby providing a track to support and maintain the position of the ball bearings 425b such that the ball bearings 425b run smoothly therebetween and freely within the bearing retainer 426a. Rotation of the inner shaft 420 results in a corresponding rotation of the bearing assembly 425.

Actuation of the inner shaft 420 rotates both the outer shaft 410 and the inner shaft 420 such that the proximal and distal adjustment assemblies 150, 170 (see e.g., FIG. 1) of the spinal implant 100 are simultaneously adjusted. When the outer shaft 410 meets a first value of resistance associated with the proximal adjustment assembly 150 (e.g., resistance due to the proximal region 100a of the spinal implant 100 contacting endplates of the vertebral bodies), the outer shaft 410 will stop rotating while the inner shaft 420 continues to rotate until the inner shaft 420 meets a second value of resistance associated with the distal adjustment assembly 170 (e.g., resistance due to the distal region 100b of the spinal implant 100 contacting the endplates of the vertebral bodies). Accordingly, the driving instrument 400 expands the spinal implant 100 to a configuration that fills the intervertebral disc space.

The simultaneous, yet independent, adjustability of the proximal and distal regions 100a, 100b of the spinal implant 100 with the driving instrument 400 allows a clinician to adjust the dimensions of the spinal implant 100 (i.e., vertical heights of the proximal and distal regions) to partially or fully expanded positions so that the upper and lower bodies 110, 130 are aligned with the endplates to maximize surface contact between the spinal implant 100 and the endplates, and to match the dimensions of the disc space defined between the endplates in which the spinal implant 100 is disposed, without force, to avoid trauma to the vertebral bodies, and in particular, the endplates of the vertebral bodies.

The driving instrument 400 may be utilized in a system including the insertion instrument 200 and the spinal implant 100 in a similar manner discussed above with regard to the driving instrument 300.

An exemplary method of inserting, positioning, and/or adjusting (e.g., expanding) the spinal implant 100 in a disc space between adjacent vertebral bodies with the insertion instrument 200 and the driving instrument 300, 400 will now be described. A clinician removes all or a portion of a disc from between two vertebral bodies (e.g., complete or partial diskectomy), and scrapes and cleans the endplates of the vertebral bodies to prepare the surfaces for placement of the spinal implant 100 such that a fusion will occur. Next, the clinician places the spinal implant 100 into the disc space using the insertion instrument 200, alone or in combination with the insertion shaft 250, by aligning and releasably securing the connector assembly 230 of the insertion instrument 200 to the spinal implant 100, as described above. The insertion instrument 200, and optionally the insertion shaft 250, may be pre-attached to the spinal implant 100 prior to inserting the spinal implant 100 into the disc space, or may be attached after the spinal implant 100 is positioned in the disc space. A slap hammer (not shown), as is known in the art, or other suitable instrument may be used with or integrated into the insertion instrument 200 or the insertion shaft 250 to facilitate placement of the spinal implant 100 into the disc space.

In one embodiment, the driving instrument 300, which is positioned in the height adjusting position "H", is inserted through the lumen 201 of the insertion instrument 200. As shown, for example, in FIG. 17C, the driving instrument 300 extends through the insertion instrument 200 such that the open tip 316 of the outer shaft 310 engages the flange nut 154 of the spinal implant 100 and the distal tip 326 of the distal inner shaft 320 engages the recessed proximal end 172b of the threaded post 172. The clinician may then move the adjustment knob 336 of the driving instrument 300 to posterior adjusting position "P" or the lordosis adjusting position "L", as described above, to actively engage/disengage the outer shaft 310 or the distal inner shaft 320 to adjust the position (i.e., height) of the proximal or distal region 100a, 100b of the spinal implant 100.

For example, as discussed above, the adjustment knob 336 of the driving instrument 300 may be moved to the posterior adjusting position "P" to actively engage the outer shaft 310 (and disengage the distal inner shaft 320) such that rotation of the proximal outer shaft 332 in a first or second direction rotates the flange nut 154 of the spinal implant 100 which, in turn, actuates the proximal adjustment assembly 150 of the spinal implant 100. The adjustment knob 336 of the driving instrument 300 may be moved to the lordosis adjusting position "L" to actively engage the distal inner shaft 320 (and disengage the outer shaft 310) such that rotation of the proximal outer shaft 332 in a first or second direction rotates the threaded post 172 which, in turn, actuates the distal adjustment assembly 170 of the spinal implant 100.

In another embodiment, the driving instrument 400 is inserted through the lumen 201 of the insertion instrument 200 such that the open tip 316 of the outer shaft 310 engages the flange nut 154 of the spinal implant 100 and the distal tip 326 of the distal inner shaft 320 engages the recessed proximal end 172b of the threaded post 172. The clinician may then rotate the inner shaft 420 to rotate both the outer and inner shafts 410, 420 simultaneously which, in turn, actuates the proximal and distal adjustment assemblies 150, 170 of the spinal implant 100 until resistance is met by each of the outer and inner shafts 410, 420, as described above, to adjust the position (e.g., the height) of the proximal and distal regions 100a, 100b of the spinal implant 100 with the disc space.

It is envisioned that a feedback mechanism (e.g., audible, tactile, etc.) may be incorporated into the insertion instrument 200 and/or the driving instrument 300, 400 to provide an indication to the clinician of expansion and/or retraction of the proximal and/or distal adjustment assemblies 150, 170 of the spinal implant 100. For example, the insertion instrument 200 and/or the driving instrument 300, 400 may include a ratchet such that each turn, or portion of a turn, produces an audible sound (e.g., a click) to alert the clinician that the spinal implant 100 is being expanded and/or retracted. Further, each audible click may represent expansion or contraction of a predetermined amount (e.g., 2 mm). Additionally or alternatively, the insertion instrument 200 and/or the driving instrument 300, 400 may include a quick release feature (e.g., that releases a ratchet) so that the surgical implant 100 can be quickly reduced.

Various allograft and/or autograft materials may be placed into and/or next to the spinal implant 100 to assist in the fusion process. By way of example, it is contemplated that a catheter or similar tubular instrument may be inserted through the lumen 201 of the insertion instrument 200 after the insertion shaft 250 or the driving instrument 300, 400 is removed. Bone or other natural or synthetic graft material may then be injected through the catheter or tubular instrument to exit at the far end of the instrument to provide graft material in and around the spinal implant 100. Should the clinician need to adjust the proximal and/or distal heights of the spinal implant 100 once it is expanded, the driving instrument 300, 400 would be re-engaged with the flange nut 154 and/or the threaded post 172 for the desired adjustment.

While the embodiments shown and described herein illustrate systems including either the driving instrument 300 or the driving instrument 400, it should be understood that a method of adjusting the spinal implant 100 may include the use of both driving instruments 300, 400.

For example, the spinal implant 100 attached to the insertion instrument 200, and optionally the insertion shaft 250, may be inserted into a disc space between vertebrae with the exterior surfaces of the upper and lower bodies 110, 130 of the spinal implant 100 substantially parallel. The driving instrument 300 or the driving instrument 400 may then be used to actuate both the proximal and distal adjustment assemblies 150, 170 of the spinal implant 100 such that the spinal implant 100 is expanded while maintaining the upper and lower bodies 110, 130 substantially parallel to one another until the vertebral bodies are engaged. Thereafter, the proximal and distal adjustment assemblies 150, 170 may be individually actuated via the driving instrument 300 to adjust the disposition of the upper and lower bodies 110, 130 to accommodate lordosis. Alternatively, after the spinal implant 100 is inserted into a disc space with the upper and lower bodies 110, 130 substantially parallel, one of the proximal or distal regions 100a, 100b of the spinal implant 100 may be expanded by actuating the corresponding proximal or distal adjustment assembly 150, 170, followed by either (i) expanding the proximal and distal regions 100a, 100b of the spinal implant 100 simultaneously to provide further parallel expansion, or (ii) expanding the other of the proximal or distal adjustment assembly 150, 170 to adjust the other region of the spinal implant 100 into contact with the vertebral bodies. Thereafter, the spinal implant 100 may be (i) locked in place with the set screw 190 as described below, (ii) further expanded or retracted in parallel by actuating the proximal and distal adjustment assemblies 150, 170 at the same time, or (iii) further adjusted to conform to the anatomy by alternately actuating one or both of the proximal and distal adjustment assemblies 150, 170.

It is further contemplated that the spinal implant 100 may be adjusted to approximate the lordosis of the patient by adjusting one or both of the proximal and distal adjustment assemblies 150, 170 prior to inserting the spinal implant 100 into the disc space, thereby approximating the pre-existing lordotic condition of the patient. After the spinal implant 100 is so adjusted and inserted, either of the driving instruments 300, 400 may then be used to actuate the proximal and distal adjustment assemblies 150, 170 such that the spinal implant 100 is expanded until the vertebral bodies are engaged. Thereafter, the proximal or distal adjustment assembly 150, 170 may be actuated to adjust the disposition of the upper and lower bodies 110, 130 of the spinal implant 100 to accommodate lordosis. Alternatively, after the spinal implant 100 is inserted with the upper and lower bodies 110, 130 predisposed for lordosis, one of the proximal or distal regions 100a, 100b of the spinal implant 100 may be expanded by actuating the corresponding proximal or distal adjustment assembly 150, 170, followed by either (i) expanding the proximal and distal regions 150, 170 of the spinal implant 100 simultaneously, or (ii) expanding the other of the proximal or distal adjustment assembly 150, 170 to adjust the other region of the spinal implant 100 into contact with the vertebral bodies. Thereafter, the spinal implant 100 may be (i) locked in place with the set screw 190, (ii) further expanded or retracted in parallel by actuating the proximal and distal adjustment assemblies 150, 170 at the same time, or (iii) further adjusted to conform to the anatomy by alternately actuating one or both of the proximal and distal adjustment assemblies 150, 170.

Figure 22:
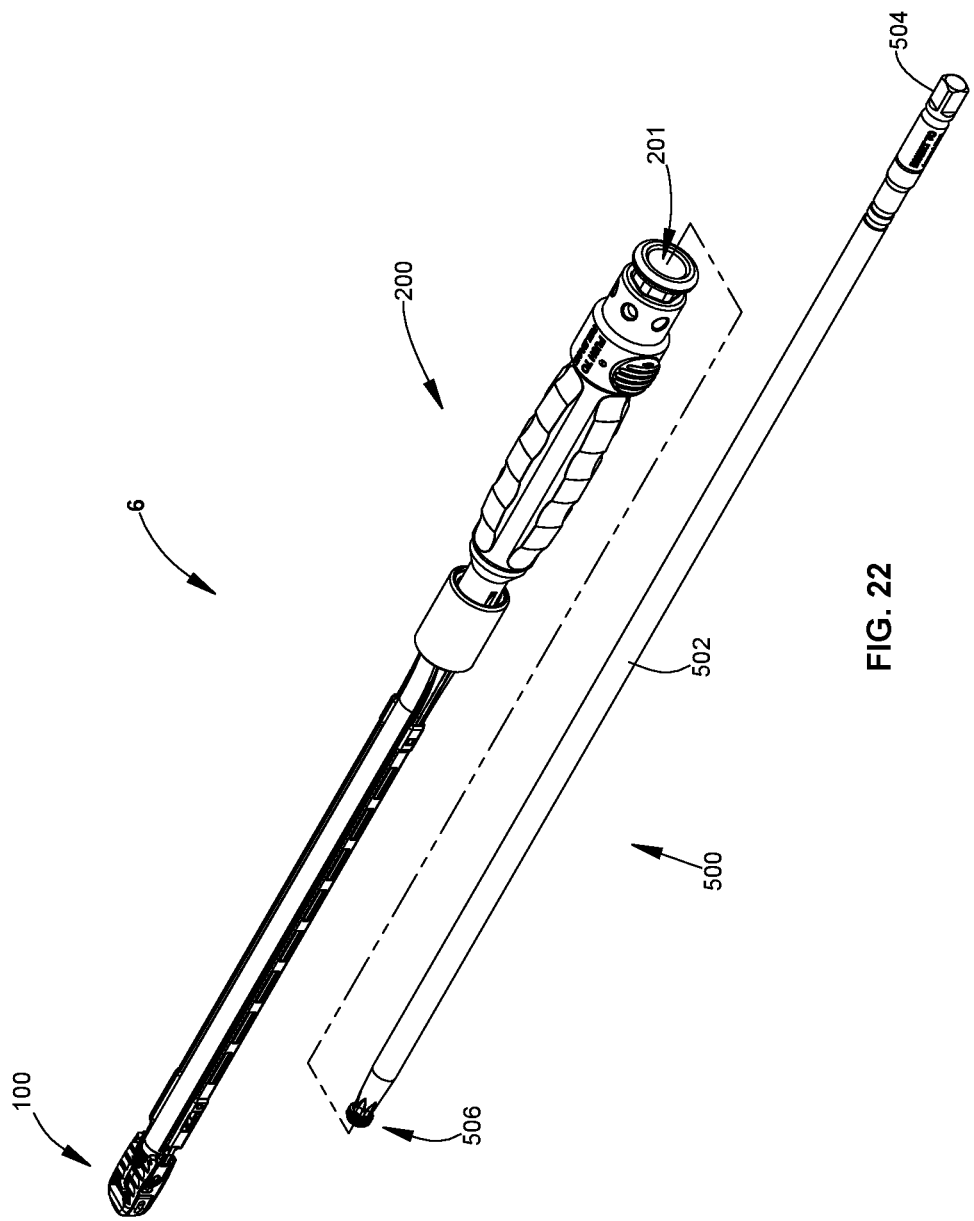
FIG. 22 is a perspective view of a system including the spinal implant and the insertion instrument of FIG. 4, and a set screw driver in accordance with another embodiment of the present disclosure.

As shown in FIG. 22, a system 6 includes the spinal implant 100, the insertion instrument 200, and a set screw driver 500. The set screw driver 500 includes an elongated body 502 having a proximal end 504 configured to engage a rotation instrument (not shown, but which may be a T-handle) and a distal end 506 configured to engage the set screw 190 (FIG. 1) of the spinal implant 100. In a method of use, the set screw driver 500, having the set screw 190 releasably attached thereto, is introduced through the lumen 201 of the insertion instrument 200 such that the set screw 190 may be screwed into the threaded inner surface 153 (FIG. 3) of the linkage body 152 to lock the spinal implant 100 in the desired position.

With reference now to FIGS. 23A-23C, an embodiment of a sleeve 600 for use in a system of the present disclosure is shown. The sleeve 600 includes an elongated sleeve body 602 extending along a longitudinal axis "Z" and defining a channel 603 therethrough. The elongated sleeve body 602 has a proximal portion 602a including a handle 604 extending therefrom in a direction that is transverse to the longitudinal axis "Z" and a distal portion 602b sized and shaped for positioning between adjacent vertebral bodies to maintain the opening of a disc space. The elongated sleeve body 602 is formed from a rigid biocompatible material, such as metals or metal alloys to provide stability to the sleeve 600, for example, during insertion into a disc space.

Figure 24C:
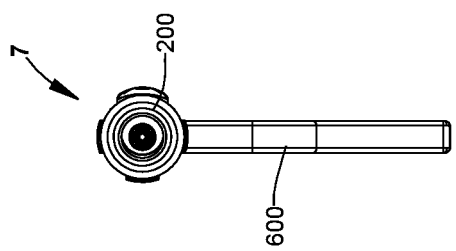
FIG. 24C is an end view of the system of FIG. 24A.
Figure 24A:
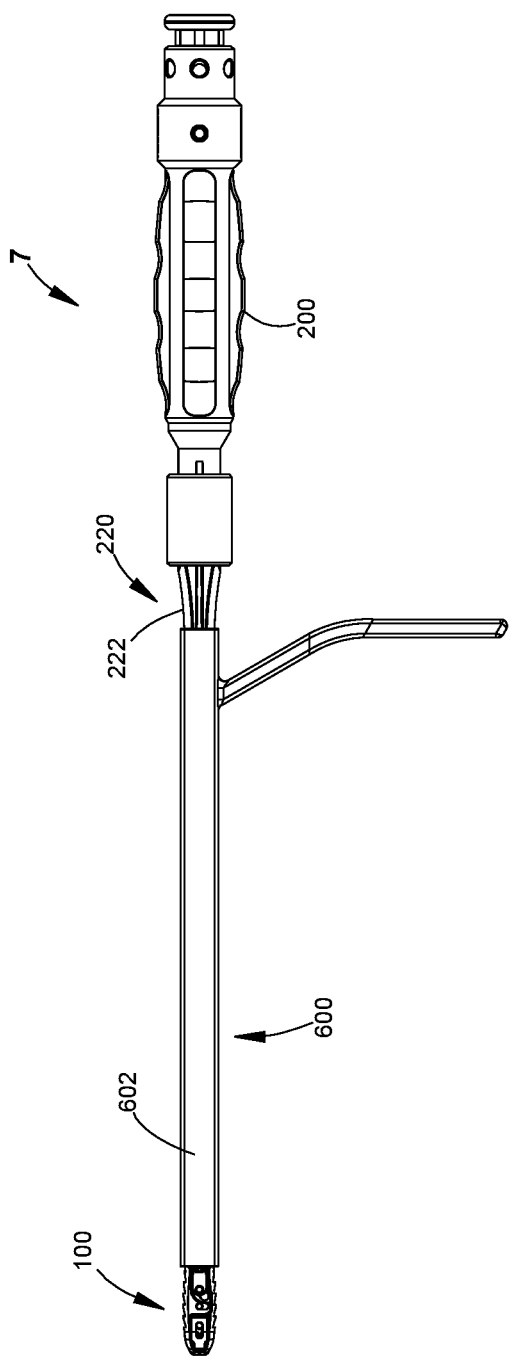
FIG. 24A is a side view of a system including the spinal implant and the insertion instrument of FIG. 4, and the sleeve of FIG. 23A in accordance with an embodiment of the present disclosure.
Figure 24B:
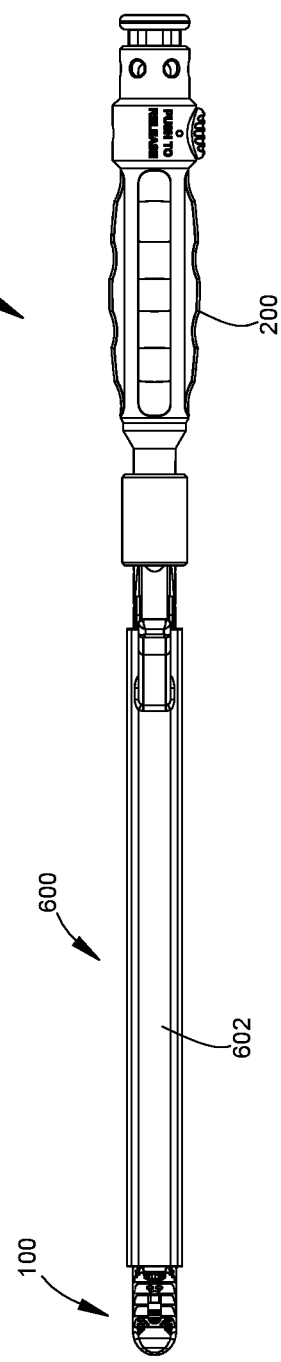
FIG. 24B is a top view of the system of FIG. 24A.

In a method of use, prior to the clinician placing the spinal implant 100 into the disc space using the insertion instrument 200, the clinician inserts the distal end 602b of the elongated sleeve body 602 between the adjacent vertebral bodies to maintain the disc space therebetween. A slap hammer (not shown) or other suitable instrument may be used to facilitate placement of the distal end 602b of the sleeve 600 therein. Thereafter, as shown in system 7 of FIGS. 24A-24C, the insertion instrument 200 is inserted through the sleeve 600 by passing the body portion 220 of the insertion instrument 200, which is attached to the spinal implant 100, distally through the channel 603 (FIG. 23C) of the elongated sleeve body 602 until the elongated shaft 222 of the insertion instrument 200 is positioned within the elongated sleeve body 602 and the spinal implant 100 extends distally therefrom into the disc space. Once the spinal implant 100 is positioned in the disc space, the clinician continues with the procedure as discussed hereinabove.

Persons skilled in the art will understand that the structures and methods specifically described herein and shown in the accompanying figures are non-limiting exemplary embodiments, and that the description, disclosure, and figures should be construed merely as exemplary of particular embodiments. By way of example, it is contemplated that the insertion instrument and/or driving instrument may be provided with indicia or other markings or references to indicate the relative position of the threaded post and/or flange nut, so that the position of the upper and lower bodies relative to one another can be understood from the positon of the instrument handles. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described.

What is claimed is:

1. A driving instrument for adjusting a spinal implant comprising:
    an outer shaft including a distal end; and
    an inner shaft disposed within the outer shaft, the inner shaft including a distal end, the distal ends of the outer and inner shafts configured to actuate respective proximal and distal adjustment assemblies of a spinal implant and a proximal end extending proximally from the outer shaft and configured to be rotated such that rotation of the inner shaft results in simultaneous rotation of the inner and outer shafts, wherein rotation of the outer shaft ceases at a first value of resistance associated with the proximal adjustment assembly and rotation of the inner shaft ceases at a second value of resistance associated with the distal adjustment assembly, such that cessation of rotation of the inner shaft is independent from cessation of rotation of the outer shaft.

2. The driving instrument according to claim 1, wherein the distal end of the outer shaft has an inner surface configured to engage a drive nut of the proximal adjustment assembly, and the distal end of the inner shaft includes an outer surface configured to engage a drive screw of the distal adjustment assembly.

3. The driving instrument according to claim 1, wherein a bearing assembly is disposed around the inner shaft and within the outer shaft.

4. The driving instrument according to claim 3, wherein the bearing assembly includes a bearing retainer having ball bearings disposed therein, and end plates positioned on opposed sides of the bearing retainer.

5. The driving instrument according to claim 1, wherein a bushing is disposed around the inner shaft and within the outer shaft.

6. The driving instrument according to claim 5, wherein a spring is disposed around the inner shaft and is partially disposed within the bushing.

7. A system for implanting a spinal implant into a disc space between adjacent vertebral bodies, the system comprising:
    a spinal implant including proximal and distal adjustment assemblies that are independently operable to change a height of a proximal or distal region, respectively, of the spinal implant; and
    a driving instrument comprising:
        an outer shaft including a distal end configured to actuate the proximal adjustment assembly of the spinal implant; and
        an inner shaft disposed within the outer shaft, the inner shaft including a distal end configured to actuate the distal adjustment assembly of the spinal implant and a proximal end extending proximally from the outer shaft and configured to be rotated such that rotation of the inner shaft results in simultaneous rotation of the inner and outer shafts to actuate both the proximal and distal adjustment assemblies, wherein rotation of the outer shaft ceases at a first value of resistance associated with the proximal adjustment assembly and rotation of the inner shaft ceases at a second value of resistance associated with the distal adjustment assembly such that cessation of rotation of the inner shaft is independent from cessation of rotation of the outer shaft.

8. The system according to claim 7, wherein the distal end of the outer shaft of the driving instrument has an inner surface configured to engage a drive nut of the proximal adjustment assembly, and the distal end of the inner shaft includes an outer surface configured to engage a drive screw of the distal adjustment assembly.

9. The system according to claim 7, wherein a bearing assembly is disposed around the inner shaft and within the outer shaft of the driving instrument.

10. The system according to claim 9, wherein the bearing assembly includes a bearing retainer having ball bearings disposed therein, and end plates positioned on opposed sides of the bearing retainer.

11. The system according to claim 7, wherein a bushing is disposed around the inner shaft and within the outer shaft of the driving instrument.

12. The system according to claim 11, wherein a spring is disposed around the inner shaft and is partially disposed within the bushing.

13. The system according to claim 7, further comprising:
    an insertion instrument comprising:
        a body portion defining a lumen therethrough configured for reception of the driving instrument therein such that the proximal end of the driving instrument extends proximally therefrom; and
        a connector assembly including connector arms pivotably secured to opposed sides of the body portion, the connector arms configured to engage an outer surface of the spinal implant.

14. The system according to claim 13, wherein the insertion instrument includes a handle having a button disposed therein, the button biased within the handle such that a slot defined through the button is axially misaligned with the lumen of the body portion, the button depressible to align the slot with the lumen.

15. The system according to claim 13, further comprising:
an insertion shaft positionable through the lumen defined through the insertion instrument, the insertion shaft having a distal end configured to engage the spinal implant.

16. The system according to claim 13, further comprising:
a set screw driver positionable through the lumen defined through the insertion instrument, the set screw driver having a distal end configured to releasably engage a set screw of the spinal implant.

17. The system according to claim 13, further comprising:
a sleeve including an elongated sleeve body defining a channel therethrough, the channel dimensioned to receive the body portion of the insertion instrument therethrough.

* * * * *